(12) United States Patent
Wun

(10) Patent No.: US 7,378,393 B2
(45) Date of Patent: May 27, 2008

(54) RECOMBINANT ANTICOAGULANT PROTEINS

(76) Inventor: Tze Chein Wun, 613 Huntley Heights Dr., Ballwin, MO (US) 63021

( * ) Notice: Subject to any disclaimer, the term of this patent is extended or adjusted under 35 U.S.C. 154(b) by 378 days.

(21) Appl. No.: 10/516,908

(22) PCT Filed: Jun. 4, 2003

(86) PCT No.: PCT/US03/17442

§ 371 (c)(1),
(2), (4) Date: Mar. 17, 2005

(87) PCT Pub. No.: WO03/103577

PCT Pub. Date: Dec. 18, 2003

(65) Prior Publication Data

US 2005/0164926 A1    Jul. 28, 2005

Related U.S. Application Data

(60) Provisional application No. 60/386,932, filed on Jun. 6, 2002.

(51) Int. Cl.
*A61K 38/00* (2006.01)
*A61K 35/14* (2006.01)
*C07K 1/00* (2006.01)
*C12Q 1/56* (2006.01)

(52) U.S. Cl. ............ 514/12; 530/380; 530/350; 435/13

(58) Field of Classification Search ............ 530/350, 530/380; 435/13; 514/12
See application file for complete search history.

(56) References Cited

FOREIGN PATENT DOCUMENTS

EP       0965597     12/1999
WO    WO 88/07676   10/1998

OTHER PUBLICATIONS

Kohler et al., Biochemisrty, 36(26), 8189-8194, 1997.*
Bach et al., Expression of tissue factor procoagulant activity: Regulation by cytosolic calcium. Proc Natl Acad Sci USA 1990; 87: 6995-9.
Bevers et al., Generation of prothrombin-converting activity and the exposure of phosphotidylserine at the outer surface of platelets. Eur J Biochem 1982; 122: 429-36.
Bombeli et al., Apoptotic vascular endothelial cells become procoagulant. Blood 1997; 89: 2429-42.
Broze, Tissue factor pathway inhibitor and the current concept of blood coagulation. Blood Coagul Fibrinol 1995; 6: 7-13.
Chase et al., Titration of trypsin, plasmin, and thrombin with *p*-nitrophenyl *p'*-guanidinobenzoate HCI. Methods Enzymol 1970; 19: 20-7.
Dachary-Prigent et al., Physiopathological significance of catalytic phospholipids in the generation of thrombin. Sem Thromb Hemost 1996; 22: 157-64.

Dennis et al., Kunitz domain inhibitors of tissue factor-factor VIIa. I. Potent inhibitors selected from libraries by phage display. J Biol Chem 1994; 269: 22129-36.
Dennis et al., Kunitz domain inhibitors of tissue factor-factor VIIa. II. Potent and specific inhibitors by competitive phage selection. J Biol Chem 1994; 269: 22137-44.
Diaz-Collier et al., Refold and characterization of recombinant tissue factor pathway inhibitor expressed in *E. coli*. Thromb Haemost 1994; 71: 339-46.
Franssen et al., Prothrombinase is protected from inactivation by tissue factor pathway inhibitor: competition between prothrombin and inhibitor. Biochem J 1997; 323: 33-7.
Gill et al., Calculation of protein extinction coefficients from amino acid sequence data. Anal Biochem 1989; 182: 319-26.
Girard et al., Inhibition of factor VIIa-tissue factor coagulation activity by a hybrid protein. Science 1990; 248: 1421-4.
Greeno et al., Apoptosis is associated with increased cell surface tissue factor procoagulant activity. Lab Invest 1996; 75: 281-9.
Hansen et al., Discordant expression of tissue factor and its activity in polarized epithelial cells. Asymmetry in anionic phospholipid availability as a possible explanation. Blood 1999; 94: 1657-64.
Haskel et al., Prevention of arterial reocclusion after thrombolysis with recombinant lipoprotein-associated coagulation inhibitor. Circulation 1991; 84: 821-7.
Hoffman et al., Factors IXa and Xa play distinct roles in tissue factor-dependent initiation of coagulation. Blood 1995; 86:1794-801.
Jang et al., Influence of blockade at specific levels of the coagulation cascade on restenosis in a rabbit atherosclerotic femoral artery injury model. Circulation 1995; 92: 3041-50.
Kinsky, Preparation of liposomes and a spectrometric assay for release of trapped glucose marker. Methods Enzymol. 1974; 32: 501-514.
Krishnaswamy et al., Role of the membrane surface in the activation of human coagulation factor X. J Biol Chem 1992; 267: 26110-20.
Le et al., Studies of the mechanism for enhanced cell surface factor VIIa/tissue factor activation of factor X on fibroblast monolayers after their exposure to N-ethylmaleimide. Thromb Haemost 1994; 72: 848-55.
Lefovits et al., Selection inhibition of factor Xa is more efficient that factor VIII tissue factor complex blockade at facilitating coronary thrombolysis in the canine model. J. Am. Coll. Cardiol. 1996; 28: 1858-65.

(Continued)

*Primary Examiner*—Maryam Monshipouri
(74) *Attorney, Agent, or Firm*—Sonnenschein Nath and Rosenthal LLP

(57) ABSTRACT

Novel recombinant anticoagulation proteins, methods of their use and methods of their production are described. In particular, recombinant fusions of annexin V (ANV) and Kunitz protease inhibitors (KPI) that possess potent anticoagulant activity are provided. The fusions, abbreviated ANV:KPI, utilize ANV having high affinity for phosphatidyl-L-serine with various KPI's to target serine proteases in membrane-associated coagulation complexes in the blood coagulation cascade. ANV:KPIs are potentially useful antithrombotic drugs permitting localized passivation of thrombogenic vessel walls and associated thrombi.

4 Claims, 5 Drawing Sheets

OTHER PUBLICATIONS

McGrath et al., Ecotin: lessons on survival in a protease-filled world. Protein Sci 1995; 4:141-8.
Mahdi et al., Protease nexin-2/amyloid beta-protein precursor inhibits factor Xa in the prothrombinase complex. J Biol Chem 1995; 270: 23468-74.
Mahdi et al., Protease nexin-2/amyloid □-protein precursor regulates factor VIIa and the factor VIIa-tissue factor complex. Thromb Res 2000; 99: 267-76.
Mann, Biochemistry and physiology of blood coagulation. Thromb Haemost 1999; 82: 165-74.
Mast et al., Physiological concentrations of tissue factor pathway inhibitor do not inhibit prothrombinase. Blood 1996; 87: 1845-50.
Monroe et al., The factor VII-platelet interplay: effectiveness of recombinant factor VIIa in the treatment of bleeding in severe thrombocytopathia. Sem Thromb Haemost 2000; 26: 373-7.
Morrisey, Tissue factor: An enzyme cofactor and a true receptor. Thromb Haemost 2001; 86: 66-74.
Neeper et al., Characterization of recombinant tick anticoagulant peptide. J. Biol. Chem. 1990; 265: 17446-52.
Petersen et al., Inhibitory properties of separate recombinant Kunitz-type-protease-inhibitor domains from tissue factor pathway inhibitor. Eur J Biochem 1996; 235, 310-6.
Rand et al., Blood clotting in minimally altered whole blood. Blood 1996; 88: 3432-45.
Reutelingsperger et al., Annexin V, the regulator of phosphatidylserine-catalyzed inflammation and coagulation. during apoptosis. Cell Mol Life Sci 1997; 53: 527-32.
Romisch et al., In vivo antithrombotic potency of placenta protein 4 (annexin V). Thromb Res 1991; 61: 93-104.
Schmaier et al., Factor IXa inhibition by protease nexin-2/amyloid beta-protein precursor on phospholipid vesicles and cell membranes. Biochemistry 1995; 34: 1171-8.
Schmaier et al., Protease Nexin-2/Amyloid β protein precursor. A tight-binding inhibitor of coagulation factor IXa. J Clin Invest 1993; 2540-5.
Scorer et al., Rapid selection using G418 of high copy number transformants of *Pichia pastoris* for high-level foreign gene expression. Biotechnology 1994; 12: 181-4.
Shi, Lactadherin inhibits enzyme complexes of blood coagulation by competing for phospholipid-binding sites. Blood 2003; 101:2628-36.
Sims et al., Unraveling the mysteries of phospholipid scrambling. Thromb Haemost 2001; 86: 266-75.
Smith, Titration of activated bovine factor X. J Biol Chem 1973; 248: 2418-23.
Smith et al., Platelet coagulation factor XIa inhibitor, a form of Alzheimer amyloid precursor protein. Science 1990; 248: 1126-8.
Stanssens et al., Anticoagulant repertoire of the hookworm *Ancylostoma caninum*. Proc Natl Acad Sci USA 1996; 93: 2149-54.
Stassen et al., Characterization of a novel series of aprotinin-derived anticoagulants. I. In vitro and pharmacological properties. Thromb Haemost 1995; 74: 646-54.
Stassen et al., Characterization of a novel series of aprotinin-derived anticoagulants. II. Comparative antithrombotic effects on primary thrombus formation in vivo. Thromb Haemost 1995; 74: 655-59.
Tait et al., Evaluation of annexin V as a platelet-directed thrombus targeting agent. Thromb Res 1994; 75: 491-501.
Thiagarajan et al., Inhibition of arterial thrombosis by recombinant annexin V in a rabbit carotid artery injury model. Circulation 1997; 96: 2339-47.
Tuszynski et al., Isolation and characterization of antistasin. J Biol Chem 1987: 262: 9718-23.
Van Ryn et al., The effect of heparin and annexin V on fibrin accretion after injury in the jugular vein of rabbit. Thromb Haemost 1993; 69: 227-30.
Waxman et al., Tick anticoagulant peptide is a novel inhibitor of blood coagulation facter Xa. Science 1990; 248: 593-6.
Wun et al., Comparison of recombinant tissue factor pathway inhibitors expressed in human SK hepatoma, mouse C127, baby hamster kidney, and Chinese hamster ovary cells. Thromb Haemost 1992; 68: 54-9.
Zwaal et al., Lipid-protein interactions in blood coagulation. Biochim Biophys Acta 1998; 1376: 433-53.
Zwaal et al., Pathophysiological implications of membrane phospholipid asymmetry in blood cells. Blood 1997; 89: 1121-32.
EMBL Database No. A01769 for "DNA Sequence (gaa) for Vascular Anticoagulating Protein," 1993, 2 pages retrieved from http://www.ebi.ac.uk/cgi-bin/emblfetch?style=html&id=A01769&Submit=Go in 2006.
Chen et al., "Fusion Proteins Comprising Annexin V and Kunitz Protease Inhibitors are Highly Potent Thrombogenic Site-Directed Anticoagulants," Blood, 2005, pp. 3902-3909, vol. 10.
Lee et al., "Protein Bifunctional Anticoagulants: Kunitz Domain-Tissue Factor Fusion Protein," Biochem., 1997, pp. 5607-5611, vol. 36.

\* cited by examiner

SEQUENCE LISTING

```
<160> NUMBER OF SEQ ID NOS: 41

<210> SEQ ID NO 1
<211> LENGTH: 382
<212> TYPE: PRT
<213> ORGANISM: Artificial
<220> FEATURE:
<223> OTHER INFORMATION: Fusion protein: human-derived ANV with TAP

<400> SEQUENCE: 1

Ala Tyr Asn Arg Leu Cys Ile Lys Pro Arg Asp Trp Ile Asp Glu Cys
1               5                   10                  15

Asp Ser Asn Glu Gly Gly Glu Arg Ala Tyr Phe Arg Asn Gly Lys Gly
            20                  25                  30

Gly Cys Asp Ser Phe Trp Ile Cys Pro Glu Asp His Thr Gly Ala Asp
        35                  40                  45

Tyr Tyr Ser Ser Tyr Asn Asp Cys Phe Asn Ala Cys Ile Gly Ser Ala
    50                  55                  60

Gln Val Leu Arg Gly Thr Val Thr Asp Phe Pro Gly Phe Asp Glu Arg
65                  70                  75                  80

Ala Asp Ala Glu Thr Leu Arg Lys Ala Met Lys Gly Leu Gly Thr Asp
                85                  90                  95

Glu Glu Ser Ile Leu Thr Leu Leu Thr Ser Arg Ser Asn Ala Gln Arg
            100                 105                 110

Gln Glu Ile Ser Ala Ala Phe Lys Thr Leu Phe Gly Arg Asp Leu Leu
        115                 120                 125

Asp Asp Leu Lys Ser Glu Leu Thr Gly Lys Phe Glu Lys Leu Ile Val
    130                 135                 140

Ala Leu Met Lys Pro Ser Arg Leu Tyr Asp Ala Tyr Glu Leu Lys His
145                 150                 155                 160

Ala Leu Lys Gly Ala Gly Thr Asn Glu Lys Val Leu Thr Glu Ile Ile
                165                 170                 175

Ala Ser Arg Thr Pro Glu Glu Leu Arg Ala Ile Lys Gln Val Tyr Glu
            180                 185                 190

Glu Glu Tyr Gly Ser Ser Leu Glu Asp Asp Val Val Gly Asp Thr Ser
        195                 200                 205

Gly Tyr Tyr Gln Arg Met Leu Val Val Leu Leu Gln Ala Asn Arg Asp
    210                 215                 220
```

```
Pro Asp Ala Gly Ile Asp Glu Ala Gln Val Glu Gln Asp Ala Gln Ala
225                 230                 235                 240

Leu Phe Gln Ala Gly Glu Leu Lys Trp Gly Thr Asp Glu Glu Lys Phe
            245                 250                 255

Ile Thr Ile Phe Gly Thr Arg Ser Val Ser His Leu Arg Lys Val Phe
                260                 265                 270

Asp Lys Tyr Met Thr Ile Ser Gly Phe Gln Ile Glu Gly Thr Ile Asp
            275                 280                 285

Arg Glu Thr Ser Gly Asn Leu Glu Gln Leu Leu Leu Ala Val Val Lys
        290                 295                 300

Ser Ile Arg Ser Ile Pro Ala Tyr Leu Ala Glu Thr Leu Tyr Tyr Ala
305                 310                 315                 320

Met Lys Gly Ala Gly Thr Asp Asp His Thr Leu Ile Arg Val Met Val
                325                 330                 335

Ser Arg Ser Glu Ile Asp Leu Phe Asn Ile Arg Lys Glu Phe Arg Lys
            340                 345                 350

Asn Phe Ala Thr Ser Leu Tyr Ser Met Ile Lys Gly Asp Thr Ser Gly
        355                 360                 365

Asp Tyr Lys Lys Ala Leu Leu Leu Ala Gly Glu Asp Asp
        370                 375                 380

<210> SEQ ID NO 2
<211> LENGTH: 378
<212> TYPE: PRT
<213> ORGANISM: Artificial
<220> FEATURE:
<223> OTHER INFORMATION: Fusion protein: human-derived ANV with
      artificial 6L15 (a variant of naturally-occurring bovine
      pancreatic trypsin inhibitor)

<400> SEQUENCE: 2

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu G

```
Phe Ile Thr Ile Phe Gly Thr Arg Ser Val Ser His Leu Arg Lys Val
            195                 200                 205

Phe Asp Lys Tyr Met Thr Ile Ser Gly Phe Gln Ile Glu Glu Thr Ile
            210                 215                 220

Asp Arg Glu Thr Ser Gly Asn Leu Glu Gln Leu Leu Ala Val Val
225                 230                 235                 240

Lys Ser Ile Arg Ser Ile Pro Ala Tyr Leu Ala Glu Thr Leu Tyr Tyr
            245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
            290                 295                 300

Gly Asp Tyr Lys Lys Ala Leu Leu Leu Ala Gly Glu Asp Asp Met
305                 310                 315                 320

His Pro Asp Phe Cys Leu Glu Pro Pro Tyr Asp Gly Pro Cys Arg Ala
            325                 330                 335

Leu His Leu Arg Tyr Phe Tyr Asn Ala Lys Ala Gly Leu Cys Gln Thr
            340                 345                 350

Phe Tyr Tyr Gly Gly Cys Leu Ala Lys Arg Asn Asn Phe Glu Ser Ala
            355                 360                 365

Glu Asp Cys Met Arg Thr Cys Gly Gly Ala
            370                 375

<210> SEQ ID NO 3
<211> LENGTH: 376
<212> TYPE: PRT
<213> ORGANISM: Artificial
<220> FEATURE:
<223> OTHER INFORMATION: Fusion protein:human-derived ANV with synthetic
      human K-APP

<400> SEQUENCE: 3

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg

```
Ala Leu Phe Gln Ala Gly Glu Leu Lys Trp Gly Thr Asp Glu Glu Lys
            180                 185                 190
Phe Ile Thr Ile Phe Gly Thr Arg Ser Val Ser His Leu Arg Lys Val
        195                 200                 205
Phe Asp Lys Tyr Met Thr Ile Ser Gly Phe Gln Ile Glu Glu Thr Ile
    210                 215                 220
Asp Arg Glu Thr Ser Gly Asn Leu Glu Gln Leu Leu Ala Val Val
225                 230                 235                 240
Lys Ser Ile Arg Ser Ile Pro Ala Tyr Leu Ala Glu Thr Leu Tyr Tyr
                245                 250                 255
Ala Met Lys Gly Ala Gly Thr Asp Asp His Thr Leu Ile Arg Val Met
            260                 265                 270
Val Ser Arg Ser Glu Ile Asp Leu Phe Asn Ile Arg Lys Glu Phe Arg
        275                 280                 285
Lys Asn Phe Ala Thr Ser Leu Tyr Ser Met Ile Lys Gly Asp Thr Ser
    290                 295                 300
Gly Asp Tyr Lys Lys Ala Leu Leu Leu Ala Gly Glu Asp Glu
305                 310                 315                 320
Val Cys Ser Glu Gln Ala Glu Thr Gly Pro Cys Arg Ala Met Ile Ser
                325                 330                 335
Arg Trp Tyr Phe Asp Val Thr Glu Gly Lys Cys Ala Pro Phe Phe Tyr
            340                 345                 350
Gly Gly Cys Gly Gly Asn Arg Asn Asn Phe Asp Thr Glu Glu Tyr Cys
        355                 360                 365
Met Ala Val Cys Gly Ser Ala Ile
    370                 375

<210> SEQ ID NO 4
<211> LENGTH: 459
<212> TYPE: PRT
<213> ORGANISM: Artificial
<220> FEATURE:
<223> OTHER INFORMATION: Fusion protein: human-derived ANV with KK-TFPI
      (a human sequence)

<400> SEQUENCE: 4

Ala Gln Val Leu Arg Gly Thr Val Thr Asp Phe Pro Gly Phe Asp Glu
1               5                   10                  15
Arg Ala Asp Ala Glu Thr Leu Arg Lys Ala Met Lys Gly Leu Gly Thr
            20                  25                  30
Asp Glu Glu Ser Ile Leu Thr Leu Leu Thr Ser Arg Ser Asn Ala Gln
        35                  40                  45
Arg Gln Glu Ile Ser Ala Ala Phe Lys Thr Leu Phe Gly Arg Asp Leu
    50                  55                  60
Leu Asp Asp Leu Lys Ser Glu Leu Thr Gly Lys Phe Glu Lys Leu Ile
65                  70                  75                  80
Val Ala Leu Met Lys Pro Ser Arg Leu Tyr Asp Ala Tyr Glu Leu Lys
                85                  90                  95
His Ala Leu Lys Gly Ala Gly Thr Asn Glu Lys Val Leu Thr Glu Ile
            100                 105                 110
Ile Ala Ser Arg Thr Pro Glu Glu Leu Arg Ala Ile Lys Gln Val Tyr
        115                 120                 125
Glu Glu Glu Tyr Gly Ser Ser Leu Glu Asp Asp Val Val Gly Asp Thr
    130                 135                 140
Ser Gly Tyr Tyr Gln Arg Met Leu Val Val Leu Leu Gln Ala Asn Arg
```

-continued

```
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190
Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240
Lys Ser Ile Arg Ser Ile Pro Ala Tyr Leu Ala Glu Thr Leu Tyr Tyr
                245                 250                 255
Ala Met Lys Gly Ala Gly Thr Asp Asp His Thr Leu Ile Arg Val Met
            260                 265                 270
Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Ala Gly Glu Asp Asp Met
305                 310                 315                 320
His Ser Phe Cys Ala Phe Lys Ala Asp Asp Gly Pro Cys Lys Ala Ile
                325                 330                 335
Met Lys Arg Phe Phe Phe Asn Ile Phe Thr Arg Gln Cys Glu Glu Phe
            340                 345                 350
Ile Tyr Gly Gly Cys Glu Gly Asn Gln Asn Arg Phe Glu Ser Leu Glu
        355                 360                 365

Glu Cys Lys Lys Met Cys Thr Arg Asp Asn Ala Asn Arg Ile Ile Lys
    370                 375                 380

Thr Thr Leu Gln Gln Glu Lys Pro Asp Phe Cys Phe Leu Glu Glu Asp
385                 390                 395                 400
Pro Gly Ile Cys Arg Gly Tyr Ile Thr Arg Tyr Phe Tyr Asn Asn Gln
                405                 410                 415
Thr Lys Gln Cys Glu Arg Phe Lys Tyr Gly Gly Cys Leu Gly Asn Met
            420                 425                 430
Asn Asn Phe Glu Thr Leu Glu Glu Cys Lys Asn Ile Cys Glu Asp Gly
        435                 440                 445

Pro Asn Gly Phe Gln Val Asp Asn Tyr Gly Thr
    450                 455

<210> SEQ ID NO 5
<211> LENGTH: 1149
<212> TYPE: DNA
<213> ORGANISM: Artificial
<220> FEATURE:
<223> OTHER INFORMATION: Fusion gene of human-derived ANV with TAP

<400> SEQUENCE: 5
gcttacaacc gtctgtgcat caaaccgcgt gactggatcg atgaatgcga ctccaacgaa      60
ggtggtgaac gtgcttactt ccgtaacggt aaaggtggtt gcgactcctt ctggatctgc     120
ccggaagacc acaccggtgc tgactactac tcctcctaca acgactgctt caacgcttgc     180
atcggatccg cacaggttct cagaggcact gtgactgact tccctggatt tgatgagcgg     240
gctgatgcag aaactcttcg gaaggctatg aaaggcttgg gcacagatga ggagagcatc     300
```

```
ctgactctgt tgacatcccg aagtaatgct cagcgccagg aaatctctgc agcttttaag    360
actctgtttg gcagggatct tctggatgac ctgaaatcag aactaactgg aaaatttgaa    420
aaattaattg tggctctgat gaaaccctct cggctttatg atgcttatga actgaaacat    480
gccttgaagg gagctggaac aaatgaaaaa gtactgacaa aaattattgc ttcaaggaca    540
cctgaagaac tgagagccat caaacaagtt tatgaagaag aatatggctc aagcctggaa    600
gatgacgtgg tggggacac  ttcagggtac taccagcgga tgttggtggt tctccttcag    660
gctaacagag accctgatgc tggaattgat gaagctcaag ttgaacaaga tgctcaggct    720
ttatttcagg ctggagaact aaatgggggg acagatgaag aaaagtttat caccatcttt    780
ggaacacgaa gtgtgtctca tttgagaaag gtgtttgaca agtacatgac tatatcagga    840
tttcaaattg aggaaaccat tgaccgcgag acttctggca atttagagca actactcctt    900
gctgttgtga aatctattcg aagtataccc gcctaccttg cagagaccct ctattatgct    960
atgaagggag ctgggacaga tgatcatacc ctcatcagag tcatggtttc caggagtgag   1020
attgatctgt taacatcag  gaaggagttt aggaagaatt ttgccacctc tctttattcc   1080
atgattaagg gagatacatc tggggactat aagaaagctc ttctgctgct cgctggagaa   1140
gatgactaa                                                           1149
```

<210> SEQ ID NO 6
<211> LENGTH: 1137
<212> TYPE: DNA
<213> ORGANISM: Artificial
<220> FEATURE:
<223> OTHER INFORMATION: Fusion gene of human-derived ANV with
      artificial 6L15, which is a variant of naturally occurring bovine
      pancreatic trypsin inhibitor

<400> SEQUENCE: 6

```
gcacaggttc tcagaggcac tgtgactgac ttccctggat tgatgagcg  ggctgatgca     60 gaaactcttc ggaaggctat gaaaggcttg gcacagatg  aggagagcat cctgactctg    120
ttgacatccc gaagtaatgc tcagcgccag gaaatctctg cagcttttaa gactctgttt    180
ggcagggatc ttctggatga cctgaaatca gaactaactg gaaaatttga aaaattaatt    240
gtggctctga tgaaaccctc tcggctttat gatgcttatg aactgaaaca tgccttgaag    300
ggagctggaa caaatgaaaa agtactgaca gaaattattg cttcaaggac acctgaagaa    360
ctgagagcca tcaaacaagt ttatgaagaa gaatatggct caagcctgga agatgacgtg    420 gtggggaca  cttcagggta ctaccagcgg atgttggtgg ttctccttca ggctaacaga    480
gaccctgatg ctggaattga tgaagctcaa gttgaacaag atgctcaggc tttatttcag    540
gctggagaac ttaatggggg acagatgaa  gaaaagttta tcaccatctt tggaacacga    600
agtgtgtctc atttgagaaa ggtgtttgac aagtacatga ctatatcagg atttcaaatt    660
gaggaaacca ttgaccgcga gacttctggc aatttagagc aactactcct tgctgttgtg    720
aaatctattc gaagtataccc tgcctacctt gcagagaccc tctattatgc tatgaaggga    780
gctgggacag atgatcatac cctcatcaga gtcatggttt ccaggagtga gattgatctg    840
tttaacatca ggaaggagtt taggaagaat tttgccacct ctctttattc catgattaag    900
ggagatacat ctggggacta taagaaagct cttctgctgc tcgctggaga agatgacatg    960
catccggact tctgcctgga accgccgtac gacggtccgt gccgtgctct gcacctgcgt   1020
tacttctaca atgcaaaggc aggcctgtgt cagaccttct actacggcgg ttgcctggct   1080
aagcgtaaca acttcgaatc cgcggaagac tgcatgcgta cttgcggtgg tgcttaa     1137
```

<210> SEQ ID NO 7
<211> LENGTH: 1131
<212> TYPE: DNA
<213> ORGANISM: Artificial
<220> FEATURE:
<223> OTHER INFORMATION: Fusion gene of human-derived ANV with synthetic human K-APP gene

<400> SEQUENCE: 7

```
gcacaggttc tcagaggcac tgtgactgac ttccctggat tgatgagcg ggctgatgca      60
gaaactcttc ggaaggctat gaaaggcttg ggcacagatg aggagagcat cctgactctg     120
ttgacatccc gaagtaatgc tcagcgccag gaaatctctg cagcttttaa gactctgttt     180
ggcagggatc ttctggatga cctgaaatca gaactaactg gaaaatttga aaaattaatt     240
gtggctctga tgaaacccctc tcggctttat gatgcttatg aactgaaaca tgccttgaag     300
ggagctggaa caaatgaaaa agtactgaca gaaattattg cttcaaggac acctgaagaa     360
ctgagagcca tcaaacaagt ttatgaagaa gaatatggct caagcctgga agatgacgtg     420
gtggggggaca cttcagggta ctaccagcgg atgttggtgg ttctccttca ggctaacaga     480
gaccctgatg ctggaattga tgaagctcaa gttgaacaag atgctcaggc tttatttcag     540
gctggagaac ttaatgggg gacagatgaa gaaaagttta tcaccatctt ggaacacga     600
agtgtgtctc atttgagaaa ggtgtttgac aagtacatga ctatatcagg atttcaaatt     660
gaggaaaccca ttgaccgcga gacttctggc aatttagagc aactactcct tgctgttgtg     720
aaatctattc gaagtatacc tgcctacctt gcagagaccc tctattatgc tatgaaggga     780
gctgggacag atgatcatac cctcatcaga gtcatggttt ccaggagtga gattgatctg     840
tttaacatca ggaaggagtt taggaagaat tttgccacct ctctttattc catgattaag     900
ggagatacat ctggggacta taagaaagct cttctgctgc tcgctggaga agatgacgag     960
gtttgttctg agcaagctga gactggtcca tgtagagcta tgatttctag atggtacttc    1020
gacgttactg agggtaagtg tgctccattc ttctacggtg gttgtggtgg taacagaaac    1080
aacttcgaca ctgaggagta ctgtatggct gtttgtggtt ctgctattta a             1131
```

<210> SEQ ID NO 8
<211> LENGTH: 1380
<212> TYPE: DNA
<213> ORGANISM: Artificial
<220> FEATURE:
<223> OTHER INFORMATION: Fusion gene of human-derived ANV with KK-TFPI, which is a human sequence

<400> SEQUENCE: 8

```
gcacaggttc tcagaggcac tgtgactgac ttccctggat tgatgagcg ggctgatgca      60
gaaactcttc ggaaggctat gaaaggcttg ggcacagatg aggagagcat cctgactctg     120
ttgacatccc gaagtaatgc tcagcgccag gaaatctctg cagcttttaa gactctgttt     180
ggcagggatc ttctggatga cctgaaatca gaactaactg gaaaatttga aaaattaatt     240
gtggctctga tgaaacccctc tcggctttat gatgcttatg aactgaaaca tgccttgaag     300
ggagctggaa caaatgaaaa agtactgaca gaaattattg cttcaaggac acctgaagaa     360
ctgagagcca tcaaacaagt ttatgaagaa gaatatggct caagcctgga agatgacgtg     420
gtggggggaca cttcagggta ctaccagcgg atgttggtgg ttctccttca ggctaacaga     480
gaccctgatg ctggaattga tgaagctcaa gttgaacaag atgctcaggc tttatttcag     540
```

```
gctggagaac ttaaatgggg gacagatgaa gaaaagttta tcaccatctt tggaacacga      600
agtgtgtctc atttgagaaa ggtgtttgac aagtacatga ctatatcagg atttcaaatt      660
gaggaaacca ttgaccgcga gacttctggc aatttagagc aactactcct tgctgttgtg      720
aaatctattc gaagtatacc tgcctacctt gcagagaccc tctattatgc tatgaaggga      780
gctgggacag atgatcatac cctcatcaga gtcatggttt ccaggagtga gattgatctg      840
tttaacatca ggaaggagtt taggaagaat tttgccacct ctctttattc catgattaag      900
ggagatacat ctggggacta taagaaagct cttctgctgc tcgctggaga agatgacatg      960
cattcatttt gtgcattcaa ggcggatgat ggcccatgta aagcaatcat gaaaagattt     1020
ttcttcaata ttttcactcg acagtgcgaa gaatttatat atgggggatg tgaaggaaat     1080
cagaatcgat ttgaaagtct ggaagagtgc aaaaaaatgt gtacaagaga taatgcaaac     1140
aggattataa agacaacatt gcaacaagaa aagccagatt tctgcttttt ggaagaagat     1200 cctgaatat gtcgaggtta tattaccagg tatttttata acaatcagac aaaacagtgt       1260
gaacgtttca gtatggtgg atcgctgggc aatatgaaca ttttgagac actggaagaa       1320 tgcaagaaca tttgtgaaga tggtccgaat ggtttccagg tggataatta tggaacctaa     1380

<210> SEQ ID NO 9
<211> LENGTH: 960
<212> TYPE: DNA
<213> ORGANISM: Homo sapiens

<400> SEQUENCE: 9
gcacaggttc tcagaggcac tgtgactgac ttccctggat ttgatgagcg ggctgatgca        60
gaaactcttc ggaaggctat gaaaggcttg ggcacagatg aggagagcat cctgactctg       120
ttgacatccc gaagtaatgc tcagcgccag gaaatctctg cagcttttaa gactctgttt       180
ggcagggatc ttctggatga cctgaaatca gaactaactg gaaaatttga aaaattaatt       240
gtggctctga tgaaaccctc tcggctttat gatgcttatg aactgaaaca tgccttgaag       300
ggagctggaa caaatgaaaa agtactgaca gaaattattg cttcaaggac acctgaagaa       360
ctgagagcca tcaaacaagt ttatgaagaa gaatatggct caagcctgga agatgacgtg       420
gtgggggaca cttcagggta ctaccagcgg atgttggtgg ttctccttca ggctaacaga       480
gaccctgatg ctggaattga tgaagctcaa gttgaacaag atgctcaggc tttatttcag       540
gctggagaac ttaaatgggg gacagatgaa gaaaagttta tcaccatctt tggaacacga       600
agtgtgtctc atttgagaaa ggtgtttgac aagtacatga ctatatcagg atttcaaatt       660
gaggaaacca ttgaccgcga gacttctggc aatttagagc aactactcct tgctgttgtg       720
aaatctattc gaagtatacc tgcctacctt gcagagaccc tctattatgc tatgaaggga       780
gctgggacag atgatcatac cctcatcaga gtcatggttt ccaggagtga gattgatctg       840
tttaacatca ggaaggagtt taggaagaat tttgccacct ctctttattc catgattaag       900
ggagatacat ctggggacta taagaaagct cttctgctgc tctgtggaga agatgactaa       960

<210> SEQ ID NO 10
<211> LENGTH: 319
<212> TYPE: PRT
<213> ORGANISM: Homo sapiens

<400> SEQUENCE: 10

Ala Gln Val Leu Arg Gly Thr Val Thr Asp Phe Pro Gly Phe Asp Glu
1               5                   10                  15
```

```
Arg Ala Asp Ala Glu Thr Leu Arg Lys Ala Met Lys Gly Leu Gly Thr
             20                  25                  30

Asp Glu Glu Ser Ile Leu Thr Leu Leu Thr Ser Arg Ser Asn Ala Gln
         35                  40                  45

Arg Gln Glu Ile Ser Ala Ala Phe Lys Thr Leu Phe Gly Arg Asp Leu
     50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
290                 295                 300

Gly Asp Tyr Lys Lys Ala Leu Leu Leu Leu Cys Gly Glu Asp Asp
305                 310                 315

<210> SEQ ID NO 11
<211> LENGTH: 33
<212> TYPE: DNA
<213> ORGANISM: Artificial
<220> FEATURE:
<223> OTHER INFORMATION: ANV reverse primer

<400> SEQUENCE: 11
atcaagctta tgcatgtcat cttctccaca gag                              33

<210> SEQ ID NO 12
<211> LENGTH: 31
<212> TYPE: DNA
<213> ORGANISM: Artificial
<220> FEATURE:
<223> OTHER INFORMATION: ANV forward primer

<400> SEQUENCE: 12
```

```
gatcggatcc agtctggtcc tgcttcacct t                               31
```

<210> SEQ ID NO 13
<211> LENGTH: 32
<212> TYPE: DNA
<213> ORGANISM: Artificial
<220> FEATURE:
<223> OTHER INFORMATION: Synthetic oligonucleotide used to generate ANV
      cDNA mutation of Cys-to-Ala at position 315

<400> SEQUENCE: 13

```
cgtgacatgc atgtcatctt ctccagcgag ca                              32
```

<210> SEQ ID NO 14
<211> LENGTH: 960
<212> TYPE: DNA
<213> ORGANISM: Artificial
<220> FEATURE:
<223> OTHER INFORMATION: Sequence encoding human ANV with Cys-to-Ala
      mutation at posiiton 315

<400> SEQUENCE: 14

```
gcacaggttc tcagaggcac tgtgactgac ttccctggat tgatgagcg ggctgatgca    60
gaaactcttc ggaaggctat gaaaggcttg gcacagatg aggagagcat cctgactctg   120
ttgacatccc gaagtaatgc tcagcgccag gaaatctctg cagcttttaa gactctgttt   180
ggcagggatc ttctggatga cctgaaatca gaactaactg gaaaatttga aaattaatt    240
gtggctctga tgaaaccctc tcggctttat gatgcttatg aactgaaaca tgccttgaag   300
ggagctggaa caaatgaaaa agtactgaca gaaattattg cttcaaggac acctgaagaa   360
ctgagagcca tcaaacaagt ttatgaagaa gaatatggct caagcctgga agatgacgtg   420
gtgggggaca cttcagggta ctaccagcgg atgttggtgg ttctccttca ggctaacaga   480
gaccctgatg ctggaattga tgaagctcaa gttgaacaag atgctcaggc tttatttcag   540
gctggagaac ttaaatgggg gacagatgaa gaaaagttta tcaccatctt tggaacacga   600
agtgtgtctc atttgagaaa ggtgtttgac aagtacatga ctatatcagg atttcaaatt   660
gaggaaacca ttgaccgcga gacttctggc aatttagagc aactactcct tgctgttgtg   720
aaatctattc gaagtatacc tgcctacctt gcagagaccc tctattatgc tatgaaggga   780
gctgggacag atgatcatac cctcatcaga gtcatggttt ccaggagtga gattgatctg   840
tttaacatca ggaaggagtt taggaagaat tttgccacct ctctttattc catgattaag   900
ggagatacat ctgggactca taagaaagct cttctgctgc tcgctggaga agatgactaa   960
```

<210> SEQ ID NO 15
<211> LENGTH: 64
<212> TYPE: DNA
<213> ORGANISM: Artificial
<220> FEATURE:
<223> OTHER INFORMATION: Synthetic oligonucleotide, first of three
      forward primers used to generate recombinant 6L15 gene

<400> SEQUENCE: 15

```
tccggacttc tgcctggaac cgccgtacga cggtccgtgc cgtgctctgc acctgcgtta    60
cttc                                                                64
```

<210> SEQ ID NO 16
<211> LENGTH: 60
<212> TYPE: DNA
<213> ORGANISM: Artificial
<220> FEATURE:

<223> OTHER INFORMATION: Synthetic oligonucleotide, second of three
      forward primers used to generate recombinant 6L15

<400> SEQUENCE: 16
tacaatgcaa aggcaggcct gtgtcagacc ttctactacg gcggttgcct ggctaagcgt     60

<210> SEQ ID NO 17
<211> LENGTH: 50
<212> TYPE: DNA
<213> ORGANISM: Artificial
<220> FEATURE:
<223> OTHER INFORMATION: Synthetic oligonucleotide, third of three
      forward primers used to generate recombinant 6L15 gene

<400> SEQUENCE: 17
aacaacttcg aatccgcgga acactgcatg cgtacttgcg gtggtgctta                50

<210> SEQ ID NO 18
<211> LENGTH: 63
<212> TYPE: DNA
<213> ORGANISM: Artificial
<220> FEATURE:
<223> OTHER INFORMATION: Synthetic oligonucleotide, first of three
      reverse primers used to generate recombinant 6L15 gene

<400> SEQUENCE: 18
acgcaggtgc agagcacggc acggaccgtc gtacggcggt tccaggcaga agtccggatg     60
cat                                                                   63

<210> SEQ ID NO 19
<211> LENGTH: 60
<212> TYPE: DNA
<213> ORGANISM: Artificial
<220> FEATURE:
<223> OTHER INFORMATION: Synthetic oligonucleotide, second of three
      reverse primers used to generate recombinant 6L15 gene

<400> SEQUENCE: 19
agccaggcaa ccgccgtagt agaaggtctg acacaggcct gcctttgcat tgtagaagta     60

<210> SEQ ID NO 20
<211> LENGTH: 60
<212> TYPE: DNA
<213> ORGANISM: Artificial
<220> FEATURE:
<223> OTHER INFORMATION: Synthetic oligonucleotide, third of three
      reverse primers used to generate recombinant 6L15 gene

<400> SEQUENCE: 20
agcttaagca ccaccgcaag tacgcatgca gtcttccgcg gattcgaagt tgttacgctt     60

<210> SEQ ID NO 21
<211> LENGTH: 177
<212> TYPE: DNA
<213> ORGANISM: Artificial
<220> FEATURE:
<223> OTHER INFORMATION: synthetic 6L15 gene

<400> SEQUENCE: 21
gctccggact tctgcctgga accgccgtac gacggtccgt gccgtgctct gcacctgcgt     60
tacttctaca atgcaaaggc aggcctgtgt cagaccttct actacggcgg ttgcctggct    120
aagcgtaaca acttcgaatc cgcggaagac tgcatgcgta cttgcggtgg tgcttaa      177

<210> SEQ ID NO 22

```
<211> LENGTH: 186
<212> TYPE: DNA
<213> ORGANISM: Artificial
<220> FEATURE:
<223> OTHER INFORMATION: Synthetic, derived from Ornithidoros moubata
      gene

<400> SEQUENCE: 22
gcttacaacc gtctgtgcat caaaccgcgt gactggatcg acgaatgcga ctccaacgaa      60
ggtggtgaac gtgcttactt ccgtaacggt aaaggtggtt gcgactcctt ctggatctgc     120
ccggaagacc acaccggtgc tgactactac tcctcctacc gtgactgctt caacgcttgc     180
atctaa                                                                186

<210> SEQ ID NO 23
<211> LENGTH: 122
<212> TYPE: DNA
<213> ORGANISM: Artificial
<220> FEATURE:
<223> OTHER INFORMATION: Forward synthetic oligonucleotide for
      generating synthetic K-APP gene with flanking sequences

<400> SEQUENCE: 23
ggccctaccc cacagatacg gagttgccac cactgaaact tgaggttgtt agagaggttt      60
gttctgagca agctgagact ggtccatgta gagctatgat ttctagatgg tacttcgacg     120
tt                                                                    122

<210> SEQ ID NO 24
<211> LENGTH: 117
<212> TYPE: DNA
<213> ORGANISM: Artificial
<220> FEATURE:
<223> OTHER INFORMATION: Forward synthetic oligonucleotide for
      generating synthetic K-APP gene with flanking sequences

<400> SEQUENCE: 24
actgagggta agtgtgctcc attcttctac ggtggttgtg gtggtaacag aaacaacttc      60
gacactgagg agtactgtat ggctgtttgt ggttctgcta tttaaatgca ttgatga        117

<210> SEQ ID NO 25
<211> LENGTH: 124
<212> TYPE: DNA
<213> ORGANISM: Artificial
<220> FEATURE:
<223> OTHER INFORMATION: Reverse synthetic oligonucleotide for
      generating synthetic K-APP gene with flanking sequences

<400> SEQUENCE: 25
ctcagtaacg tcgaagtacc atctagaaat catagctcta catggaccag tctcagcttg      60
ctcagaacaa acctctctaa caacctcaag tttcagtggt ggcaactccg tatctgtggg     120
gtag                                                                  124

<210> SEQ ID NO 26
<211> LENGTH: 115
<212> TYPE: DNA
<213> ORGANISM: Artificial
<220> FEATURE:
<223> OTHER INFORMATION: Reverse synthetic oligonucleotide for
      generating synthetic K-APP gene with flanking sequences

<400> SEQUENCE: 26
agcttcatca atgcatttaa atagcagaac cacaaacagc catacagtac tcctcagtgt      60
```

```
cgaagttgtt tctgttacca ccacaaccac cgtagaagaa tggagcacac ttacc         115
```

<210> SEQ ID NO 27
<211> LENGTH: 174
<212> TYPE: DNA
<213> ORGANISM: Artificial
<220> FEATURE:
<223> OTHER INFORMATION: Synthetic K-APP gene, derived from human
      sequence

<400> SEQUENCE: 27

```
gaggtttgtt ctgagcaagc tgagactggt ccatgtagag ctatgatttc tagatggtac    60
ttcgacgtta ctgagggtaa gtgtgctcca ttcttctacg gtggttgtgg tggtaacaga   120
aacaacttcg acactgagga gtactgtatg gctgtttgtg gttctgctat ttaa         174
```

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28

```
ggaattccat atggcacagg ttctcagagg                                     30
```

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29

```
ccaatgcatg tcatcttctc cagc                                           24
```

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30

```
ccaatgcatc cggacttctg cctg                                           24
```

<210> SEQ ID NO 31
<211> LENGTH: 24
<212> TYPE: DNA
<213> ORGANISM: Artificial
<220> FEATURE:
<223> OTHER INFORMATION: primer

<400> SEQUENCE: 31

```
ccaatgcatt cattttgtgc attc                                           24
```

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32

```
acgcgtcgac ttaagcacca ccgcaag                                        27
```

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
acgcgtcgac ttaggttcca taattatcc                                29

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
ggaattccat atggcttaca accgtctgtg                               30

<210> SEQ ID NO 35
<211> LENGTH: 27
<212> TYPE: DNA
<213> ORGANISM: Artificial
<220> FEATURE:
<223> OTHER INFORMATION: primer

<400> SEQUENCE: 35
cgggatccga tgcaagcgtt gaagcag                                  27

<210> SEQ ID NO 36
<211> LENGTH: 26
<212> TYPE: DNA
<213> ORGANISM: Artificial
<220> FEATURE:
<223> OTHER INFORMATION: primer

<400> SEQUENCE: 36
cgggatccgc acaggttctc agaggc                                   26

<210> SEQ ID NO 37
<211> LENGTH: 29
<212> TYPE: DNA
<213> ORGANISM: Artificial
<220> FEATURE:
<223> OTHER INFORMATION: primer

<400> SEQUENCE: 37
acgcgtcgac ttagtcatct tctccagcg                                29

<210> SEQ ID NO 38
<211> LENGTH: 31
<212> TYPE: DNA
<213> ORGANISM: Artificial
<220> FEATURE:
<223> OTHER INFORMATION: Primer designed for generating PCR fragment of
      interest for cloning into vector pPIC9

<400> SEQUENCE: 38
ccgctcgaga aaagagcaca ggttctcaga g                             31

<210> SEQ ID NO 39
<211> LENGTH: 33
<212> TYPE: DNA
<213> ORGANISM: Artificial
<220> FEATURE:

-continued

```
<223> OTHER INFORMATION: Primer designed for generating PCR fragment of
      interest for cloning into yeast expression vector pPIC9

<400> SEQUENCE: 39
ataagaatgc ggccgcttaa atagcagaac cac                                   33

<210> SEQ ID NO 40
<211> LENGTH: 24
<212> TYPE: DNA
<213> ORGANISM: Artificial
<220> FEATURE:
<223> OTHER INFORMATION: Primer designed for generating PCR fragment of
      interest for cloning into yeast expression vector pPIC9

<400> SEQUENCE: 40
cgcgatatca tcttctccag cgag                                             24

<210> SEQ ID NO 41
<211> LENGTH: 20
<212> TYPE: DNA
<213> ORGANISM: Artificial
<220> FEATURE:
<223> OTHER INFORMATION: Primer designed for generating PCR fragment of
      interest for cloning into yeast expression vector pPIC9

<400> SEQUENCE: 41
gaggtttgtt ctgagcaagc                                                  20
```

RECOMBINANT ANTICOAGULANT PROTEINS

This application is a national stage entry of PCT/US03/17442 filed Jun. 4, 2003, which claims priority from provisional U.S. Application No. 60/386932, filed Jun. 6, 2002, the disclosure of which is herein incorporated by reference in its entirety.

BACKGROUND OF THE INVENTION

The present invention relates in general to anticoagulant proteins, and in particular to novel recombinant blood coagulation inhibitors.

Tissue factor (TF) is generally considered to be the physiological trigger of the blood coagulation in normal hemostasis and in a variety of coagulopathic and thrombotic diseases. TF is an integral membrane protein that is normally present on the surface of certain extra-vascular cell types, but can also be induced to express on endothelium and monocytes upon stimulation [reviewed in (1)]. Based on studies in whole blood and re-constituted plasma systems (2-5), the key events of TF-initiated blood clotting can be schematically illustrated as in FIG. 1. Upon exposure, TF forms a complex with factor VII/VIIa present in the circulating blood. The resulting extrinsic tenase complex (TF/VIIa) initiates the clotting cascade by activating small amounts of factors IX and X on the TF-bearing cells/microparticles. The TF/VIIa-activated factors IXa and Xa play distinct roles in the subsequent coagulation reactions. In a complex with factor Va/V on TF-bearing membrane surface, factor Xa generates a small amount of thrombin that partially activates platelets, cleaves fibrinogen to form an initial clot, and converts factors V, VIII, and XI to their active forms. Subsequent to this initiation phase, propagation of thrombin generation begins. During the propagation phase, activated platelets provide an anionic membrane surface for the assembly of intrinsic tenase (VIIIa/IXa) and prothrombinase (Va/Xa) complexes, which very efficiently activate factor X and prothrombin, respectively, leading to explosive thrombin generation and consolidation of the fibrin-platelet plug. Three plasma anticoagulant systems regulate the clotting cascade, each acting at a different point in the cascade. Tissue factor pathway inhibitor (TFPI) influences the initiation phase by forming a TFPI-Xa inhibitory complex that inhibits TF/VIIa through feedback inhibition; antithrombin III (AT III) primarily exerts its effect by inhibiting free thrombin and Xa in the propagation phase; and activated protein C (APC) affects the duration of the propagation by proteolytically inactivating Va and VIIIa.

The availability of anionic phospholipid, chiefly phosphatidyl-L-serine (PS), is important for the assembly and expression of catalytic activities of the membrane-associated coagulation enzyme complexes (extrinsic tenase, intrinsic tenase, prothrombinase and XIa) that drive the initiation and propagation of the coagulation cascade. Plasma membrane phospholipids of mammalian cells are normally asymmetrically distributed, with PS being exclusively sequestered in the inner membrane leaflet (6). Because of PS sequestration, intact quiescent cells are normally not procoagulant. In circumstances of cell activation, cell injury, or in response to apoptotic stimuli, phospholipid asymmetry across the plasma membrane collapses, resulting in exposure of PS on the membrane surface and shedding of membrane "microparticles". The exposure of PS allows assembly of enzyme/cofactor complexes and interaction with their substrates on the membrane surface, thereby enhancing the efficiency of the coagulation reactions (7-9). TF/VII(a) complex formed on intact cells is often cryptic in enzymatic activity towards its substrates. A many fold increase in TF/VIIa activity (de-encryption) is observed when PS becomes available on the membrane surface after cell disruption, treatments with various agents, or induction of apoptosis (10-14). The rate of factor X activation by TF reconstituted with vesicles composed of phosphatidylcholine (PC) alone is less than 5% of that observed with PS-PC vesicles (15). These observations suggest that concomitant expression of TF and exposure of PS on the membrane surface are important in the initiation of coagulation. In the processes of hemostasis/thrombosis, platelets are known to provide an anionic membrane surface for the assembly of intrinsic tenase (VIIIa/IXa) and prothrombinase (Va/Xa) (7,16). Upon platelet activation, PS rapidly appears on the platelet membrane surface. Interaction of factor VIIIa with the anionic lipid creates a $Ca^{++}$-dependent high-affinity binding site for factor IXa, leading to the formation of the intrinsic tenase complex. Likewise, binding of factor Va to anionic lipid promotes $Ca^{++}$-dependent binding of factor Xa, forming the prothrombinase complex. Factor XIa also depends on the PS-exposed membrane for efficient catalysis of the conversion of factor IX into factor IXa.

TFPI is a multivalent Kunitz-type inhibitor that regulates the initiation of the tissue factor pathway of coagulation in the human vascular system (17). TFPI inhibits factor Xa directly, and in a factor Xa-dependent manner, produces a feedback inhibition of TF/VIIa complex and thus dampens the protease cascade of the tissue factor pathway. Although TFPI is physiologically very important in the regulation of tissue factor pathway, its development for clinical antithrombotic therapy is currently limited by the large doses required for it to effectively interrupt vascular thrombosis (18-20).

Several other, naturally occurring Kunitz-type inhibitors that bind factors VIIa, IXa, Xa, and XIa of the tissue factor pathway have also been described. These include leech-derived Antistasin (ATS) (21), Tick Anticoagulant Peptide (TAP) (22), and two Ancylostoma caninum Anticoagulant Peptides (AcAP5 and AcAP6) (23) that inhibit factor Xa specifically; another Ancylostoma caninum Anticoagulant Peptide (AcAPc2) that inhibits VIIa (23); and a Kunitz-inhibitory domain of amyloid β-protein precursor ($K_{APP}$) that inhibits factors VIIa, IXa, Xa, and XIa (24-27). Using site-specific mutagenesis and phage display technology, two series of $K_{APP}$ and aprotinin (bovine pancreatic trypsin inhibitor) homologs with very high affinity (sub-nanomolar $K_i$) toward different coagulation proteases (TF/VIIa, Xa, XIa, and Kallikrein etc.) have been created (28-31). However, the anticoagulant potencies of these mutants are quite low in in vitro coagulation assays (tissue factor-initiated clotting and activated partial thromboplastin time). The aprotinin homologs also require very high doses to achieve antithrombotic effect in an in vivo vascular trauma model (31).

BRIEF SUMMARY OF THE INVENTION

In accordance with the present invention, novel recombinant anticoagulant proteins, methods and materials relating to their production, and methods of their use in treatment are provided.

A novel series of recombinant anticoagulant fusion proteins are preferably created by linking annexin V (ANV) (SEQ ID NO: 10), a phosphatidylserine (PS) binding protein, to Kunitz-type protease inhibitors (KPI) targeting the serine proteases in the enzymatic complexes. The resulting fusion proteins exhibit much stronger anticoagulant activities than their component proteins. Several of these constructs possess far greater potencies than TFPI, the natural inhibitor of TF-initiated coagulation in blood. The annexinV:Kunitz-type inhibitor (ANV:KPI) fusions represent a new class of anticoagulants that specifically target the coagulation enzyme complexes on the procoagulant PS-exposed membrane surface, and are useful as anti-thrombotic therapeutic agents with an ability to passivate thrombogenic vessel wall and associated thrombi.

Therefore, in one embodiment there are provided recombinant anticoagulant proteins, each comprising a fusion of annexin V (ANV) (SEQ ID NO: 10) and a Kunitz protease inhibitor (KPI). Alternative embodiments of the recombinant anticoagulant protein include, for example, fusion of ANV with Tick Anticoagulant Peptide (TAP) (SEQ ID NO: 1), with a variant of aprotinin (6L15) (SEQ ID NO: 2), with the Kunitz-inhibitory domain of amyloid β-protein precursor ($K_{APP}$) (SEQ ID NO: 3), and with $KK_{TFI\ 22\text{-}160}$ (SEQ ID NO: 4).

In another embodiment there is provided an antithrombotic composition comprising a recombinant anticoagulant protein comprising a fusion of annexin V (ANV) (SEQ ID NO: 10) and a Kunitz protease inhibitor (KPI). Alternative embodiments of the antithrombotic composition include, for example, TAP-ANV (SEQ ID NO: 1), ANV-6L1 5 (SEQ ID NO: 2), ANV-$K_{APP}$ (SEQ ID NO: 3), and ANV-$KK_{TFPI\ 22\text{-}160}$ (SEQ ID NO: 4)

In another embodiment there is provided a method of inhibiting blood coagulation in a mammalian subject comprising administering to the subject an effective amount of a recombinant anticoagulant protein comprising a fusion of annexin V (ANV) (SEQ ID NO: 10) and a Kunitz protease inhibitor (KPI).

In another embodiment there is provided a method of producing a recombinant anticoagulant protein comprising linking annexin V (ANV) (SEQ ID NO: 10) and a Kunitz protease inhibitor (KPI).

In another embodiment there is provided a method of treating or preventing an excess of thrombotic activity in a subject in need of such treatment or prevention, said method comprising administering to the subject an effective amount of an antithrombotic composition comprising a fusion of annexin V (ANV) (SEQ ID NO: 10) and a Kunitz protease inhibitor (KPI).

In another embodiment there is provided a recombinant DNA molecule comprising a first DNA sequence encoding annexin V (ANV) (SEQ ID NO: 9) and second DNA sequence encoding a Kunitz protease inhibitor (KPI). Alternative embodiments of the recombinant DNA molecule include, for example, DNA sequences selected from the group consisting of TAP-ANV (SEQ ID NO: 5), ANV-6L15 (SEQ ID NO: 6), ANV-$K_{APP}$ (SEQ ID NO: 7), and ANV-$KK_{TFPI}$ (SEQ ID NO: 8), or conservatively substituted variants thereof.

In another embodiment there is provided a process for the preparation of a cell line expressing a recombinant anticoagulant protein comprising a fusion of annexin V (ANV) (SEQ ID NO: 10) and a Kunitz protease inhibitor (KPI), the process comprising stably transfecting a host cell with a recombinant expression vector comprising a cDNA sequence encoding ANV or conservatively substituted variants thereof, and a cDNA sequence encoding a KPI.

In another embodiment there is provided a recombinant expression vector comprising a first nucleotide sequence encoding annexin V (ANV) (SEQ ID NO: 9), $Cys^{315}$-to-Ala mutation of ANV (SEQ ID NO: 14), or conservatively substituted variants thereof, and a second nucleotide sequence of a Kunitz protease inhibitor (KPI) together with additional sequences capable of directing the synthesis of a recombinant anticoagulant protein comprising a fusion of ANV and a KPI, in a culture of stably tranfected cells. Alternative embodiments of the recombinant expression vector include, for example, a nucleotide sequence selected from the group of TAP-ANV (SEQ ID NO: 5), ANV-6L15 (SEQ ID NO: 6), ANV-$K_{APP}$ (SEQ ID NO: 7), and ANV-$KK_{TFPI}$ (SEQ ID NO: 8), or conservatively substituted variants thereof

Factor VII binds to TF and is activated to VIIa on the TF-bearing cells/microparticles. The TF/VIIa complex activates both factor IX and factor X. The factor Xa generates a small amount of thrombin (IIa) locally. This small amount of thrombin activates platelets, activates factor V, releases factor VIII from von Willebrand factor and activates it, and activates factor XI. TF/VIIa-activated IXa can then bind to the VIIa on the activated platelet to form an intrinsic tenase (VIIIa/IXa) that activates factor X efficiently. The platelet-generated Xa binds Va to form a prothrombinase (Va/Xa) that promotes large-scale conversion of prothrombin (II) to thrombin. Three plasma anticoagulant systems regulate the coagulation cascade: TFPI directly inhibits Xa, and in a Xa-dependent manner produces a feedback inhibition of TF/VIIa; AT III mainly inhibits Xa and thrombin; and APC proteolytically inactivates Va and VIIIa. Adapted from Roberts et al. (5) and Mann K et al. (3).

Figure 1:
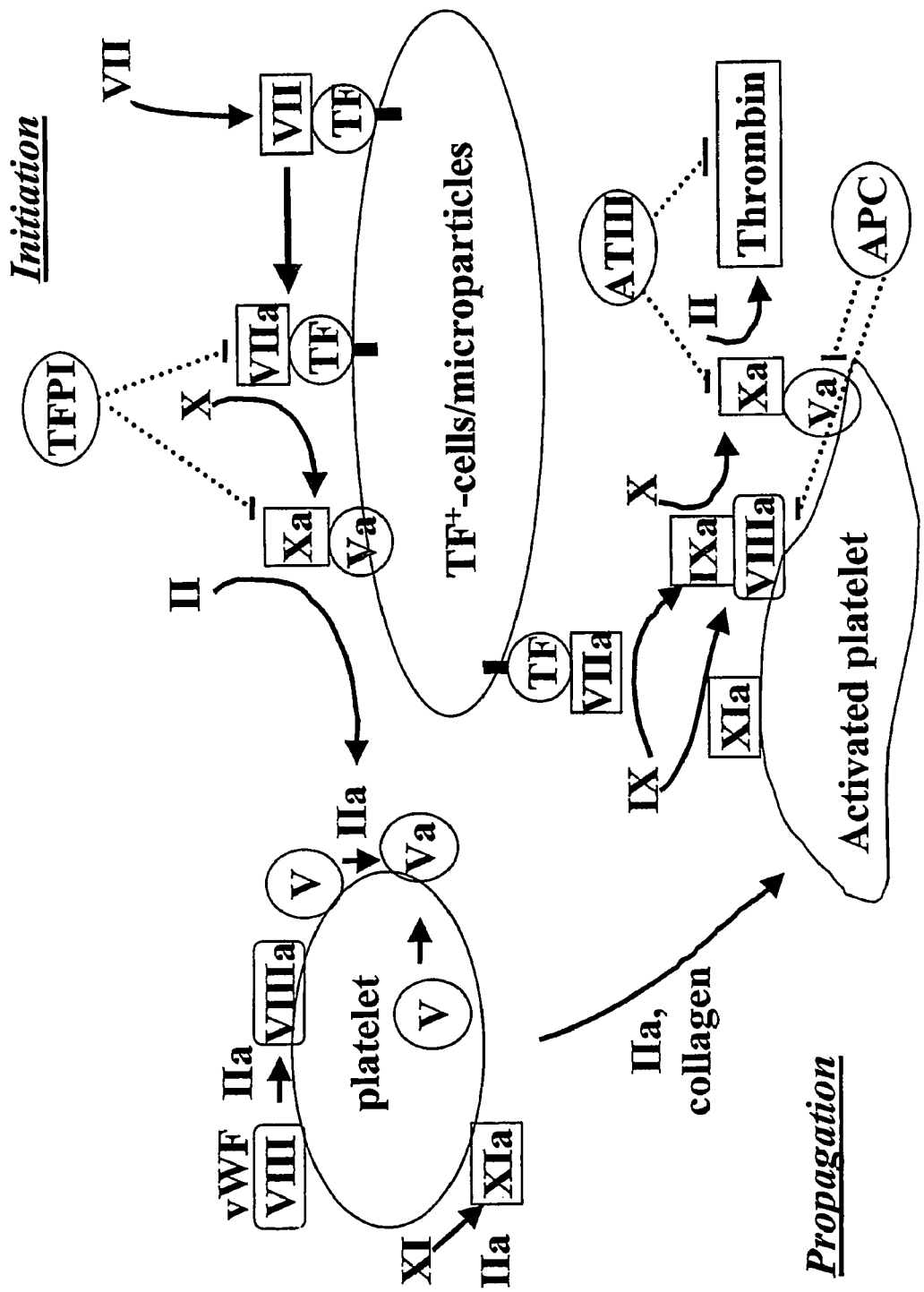
FIG. 1. Schematic of TF-initiated clotting.
Figure 2:
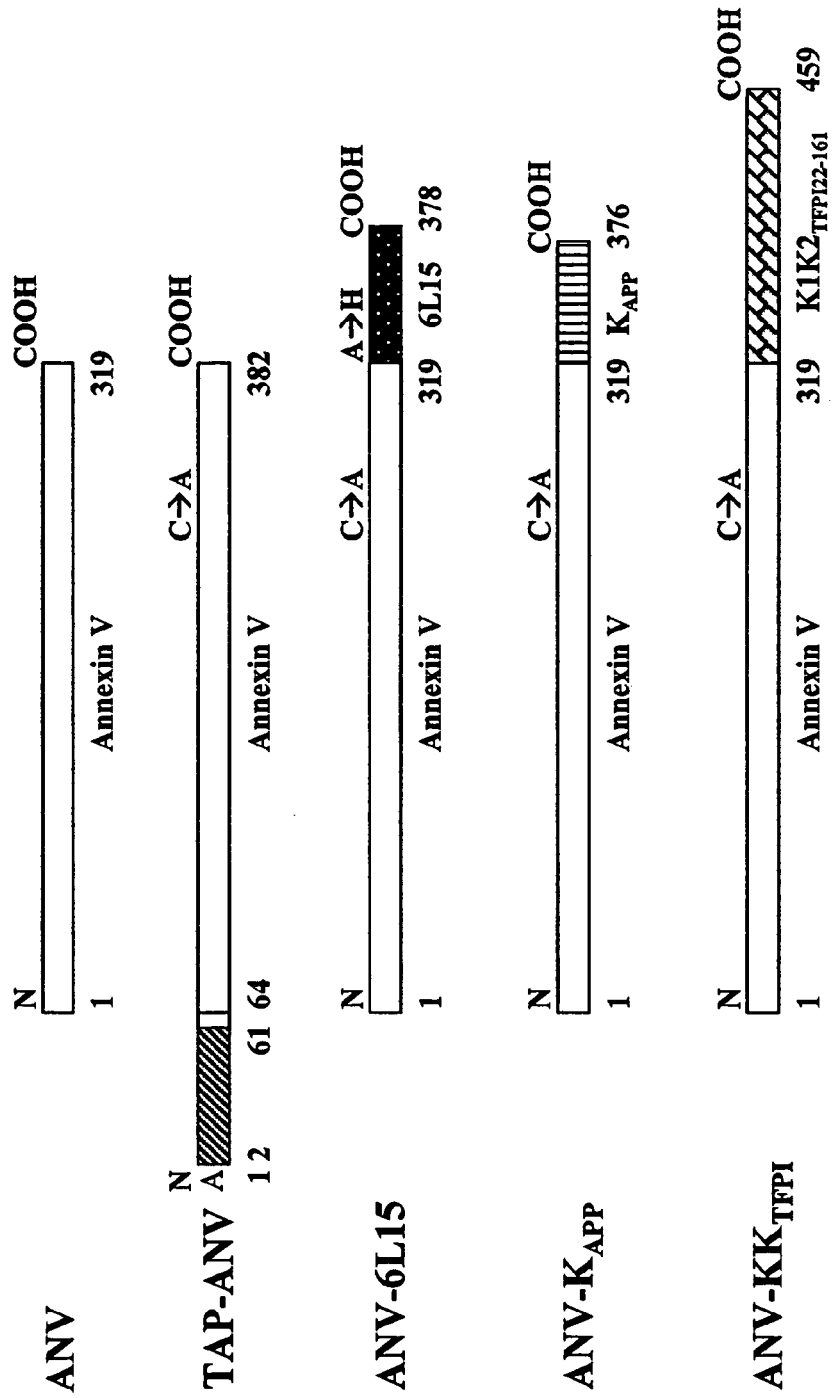

FIG. 2. Schematic of annexin V and its fusion products with various Kunitz-type inhibitors.

ANV, annexin V (SEQ ID NO: 10); TAP-ANV (SEQ ID NO: 1), ala-tick anticoagulant peptide linked to annexin V by Gly-Ser dipeptide; ANV-6L15 (SEQ ID NO: 2), annexin V linked to 6L15 (a Kunitz inhibitor with high affinity for TF/VIIa); ANV-$K_{APP}$ (SEQ ID NO: 3), annexin V linked to $K_{APP}$ (Kunitz inhibitory domain of amyloid β-protein precursor); ANV-$KK_{TFPI}$ (SEQ ID NO: 4), annexin V linked to $KK_{TFPI}$ ($TFPI_{22\text{-}161}$ containing Kunitz-1 and Kunitz-2 domains).

Figure 3:
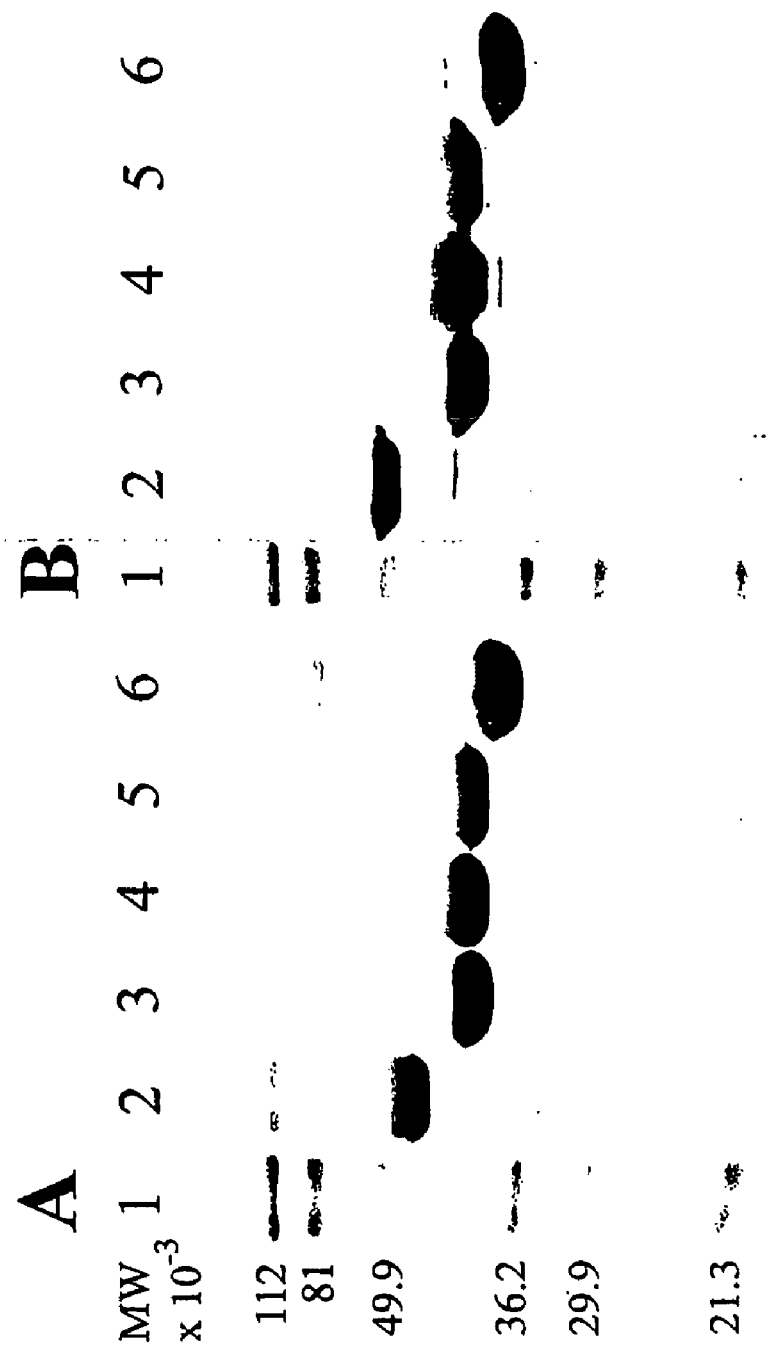

FIG. 3. SDS-PAGE analysis of purified ANV and its fusion products with various Kunitz-type protease inhibitors.

Samples were analyzed by 12% SDS-PAGE under non-reducing (A) or reducing (B) conditions followed by Coomassie blue staining. All samples were boiled for 3 min without (A), or with (B) 50 nM dithiothreotol. Approximately 5 μg proteins were loaded on each lane. Lane 1, molecular weight marker; lane 2, ANV-$KK_{TFPI}$ (SEQ ID NO: 4); lane 3, ANV-6L15 (SEQ ID NO: 2); lane 4, TAP-ANV (SEQ ID NO: 1); lane 5 ANV-$K_{APP}$ (SEQ ID NO: 3); lane 6, ANV (SEQ ID NO: 10).

Figure 4:
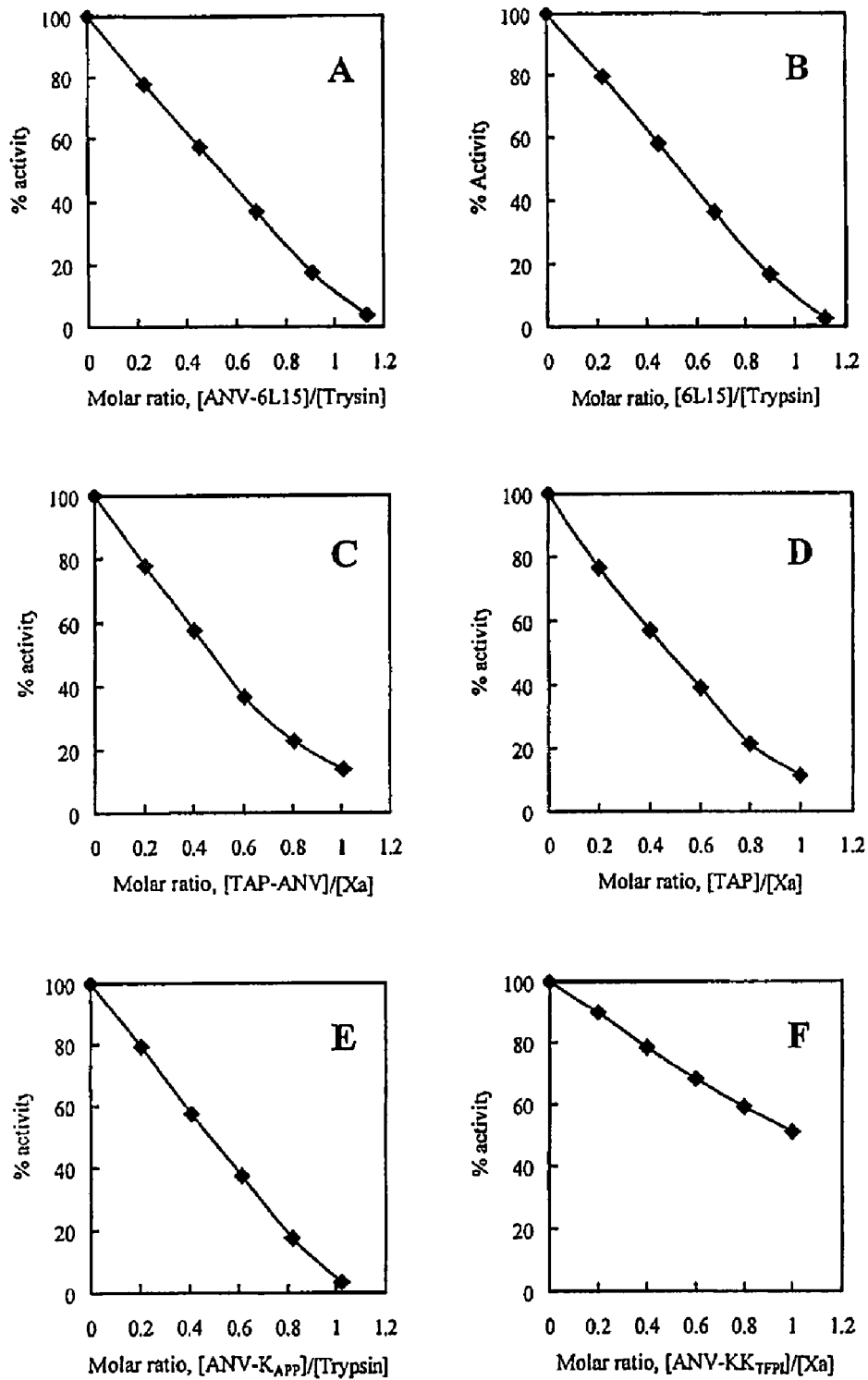

FIG. 4. Inhibition of porcine trypsin and bovine factor Xa by various purified inhibitors.

Inhibitions of trypsin and bovine factor X were measured by amidolytic assays as described in Methods herein below. The concentrations of active trypsin and bovine factor Xa were determined by active site titration with 4-nitrophenyl p'-guanidinobenzoate (41,42). The concentrations of purified inhibitors were determined by absorbance measurement at 280 nm using molar extinction coefficients of 28170, 7120, 39550, 18500, 31300, and 30170 for ANV-6L15, 6L15, TAP-ANV, TAP, ANV-$K_{APP}$, and ANV-$KK_{TFPI}$, respectively. (A) Inhibition of trypsin by ANV-6L15; (B)

Inhibition of trypsin by 6L15; (C) Inhibition of factor Xa by TAP-ANV; (D) Inhibition of factor Xa by TAP; (E) Inhibition of trypsin by ANV-K$_{APP}$; (F) Inhibition of factor Xa by ANV-KK$_{TFPI}$.

Figure 5:
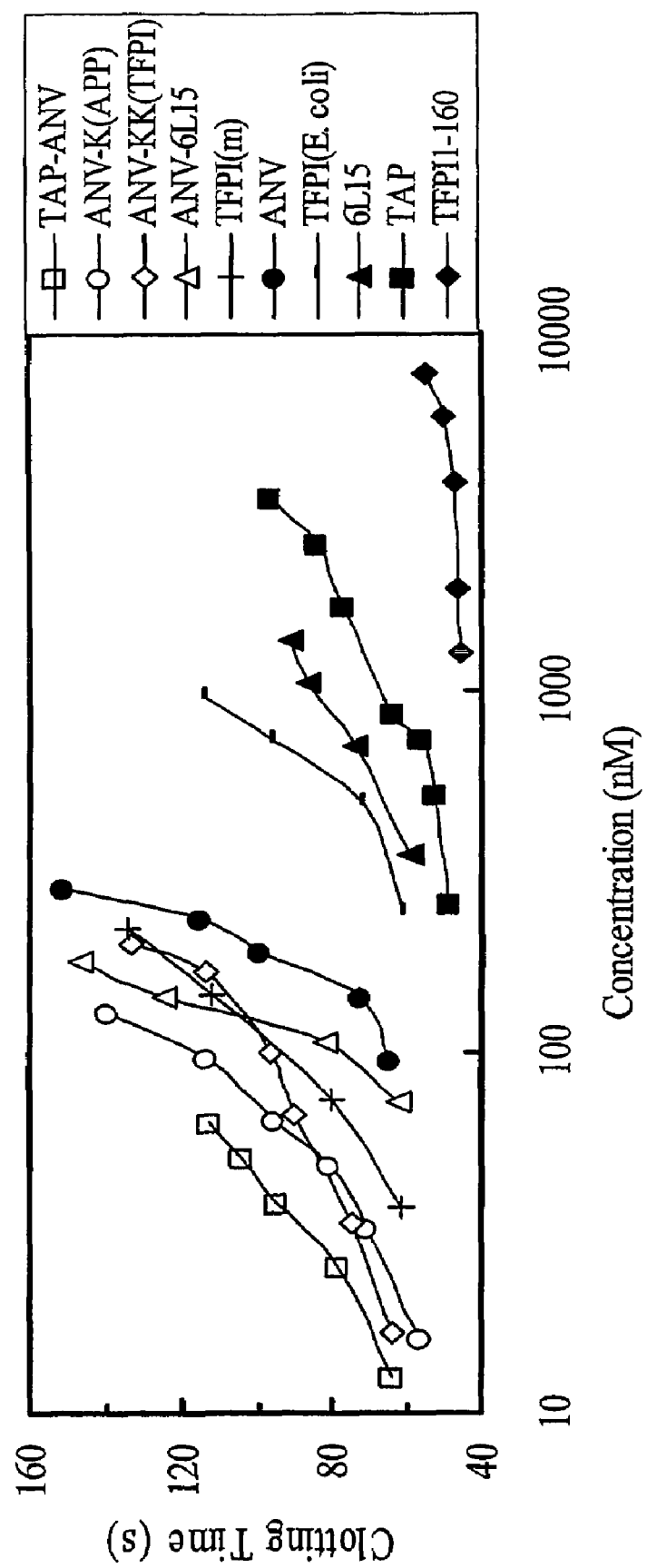

FIG. 5. Effects of various inhibitors in activated partial thromboplastin time (APTT) assay.

APTT assay was carried out using an ACL 200 Coagulometer and APTT-SP reagent (Instrument Laboratories). Pooled human plasma (180 µl) was mixed with 20 µl of various inhibitors to attain the indicated final concentrations for the assay. The plasma with control buffer had a clotting time of 40.7 sec. TFPI (m) refers to mammalian C127 cell-derived FL-TFPI.

DETAILED DESCRIPTION OF THE INVENTION

The following detailed description of the invention taken in conjunction with the accompanying drawings is provided to further illustrate the invention and preferred embodiments in greater detail.

The blood coagulation cascade proceeds primarily via the formation of coagulation enzyme complexes, each consisting of a serine protease associated with a membrane-bound cofactor/receptor on an anionic membrane surface. These complexes are conventionally named extrinsic tenase (factor VIIa-tissue factor), intrinsic tenase (factor IXa-factor VIIIa), proturombinase (factor Xa-factor Va) and XIa complex.

As described herein, a novel series of recombinant anticoagulant fusion proteins are created, for example, by linking annexin V (ANV) (SEQ ID NO: 10), a phosphatidylserine (PS) binding protein, to a Kunitz-type protease inhibitor (KPI) targeting the serine proteases in the enzymatic complexes. The resulting fusion proteins exhibit much stronger anticoagulant activities than their component proteins alone or even additively. For convenience, these recombinant anticoagulant fusion proteins are abbreviated ANV:KPI. These fusion proteins utilize the high affinity of ANV for phosphatidyl-L-serine (PS) (32) and various KPI's for inhibition of the serine proteases in membrane-associated coagulation complexes in the blood coagulation cascade. Several of these novel constructs possess far greater potencies than TFPI, the natural inhibitor of TF-initiated coagulation in blood. The annexinV:Kunitz-type protease inhibitor (ANV:KPI) fusion proteins represent a new class of anticoagulants that specifically target the coagulation enzyme complexes on the procoagulant PS-exposed membrane surface, and are useful as anti-thrombotic therapeutic agents with an ability to passivate thrombogenic vessel wall and associated thrombi. The novel fusion proteins will be useful in the treatment of diseases and conditions involving an excess of thrombogenesis, including arterial thrombotic events such as unstable angina, myocardial infarction, sudden cardiac death, ischemic stroke, ruptured aneurysms, intermittent claudication, and critical limb ischemia; venous thrombosis such as deep venous thrombosis, pulmonary embolism, thrombophlebitis, and chronic venous insufficiency; and other clinical conditions such as surgical thrombosis, prosthetic heart valve, atherosclerosis, restenosis, ischemia reperfusion injury, sepsis, disseminated intravascular coagulation, acute lung injury, malignancy, chronic renal failure, nephuotic syndrome, crescentic glomerulonephritis, diabetes, sickle cell anemia, thalassemia, antiphospholipid syndrome, extra-corporeal circulation, hemodialysis, peritoneal dialysis and annexinopathies.

In order to further illustrate the invention, the following specific laboratory examples were carried out although it will be understood that the invention is not limited to these specific examples or the details described therein.

EXAMPLES

Materials and Methods

Reagents

Urea (sequenal grade) and Brij 35 were obtained from Pierce. Mixed bed resin AG501-X8, SDS-PAGE reagents, and molecular weight markers were purchased from Bio-Rad. Dade Innovin® was from Baxter Diagnostics Inc. (Deerfield, Ill.). APTT-SP was from Instrumentation Laboratory (Lexington, Mass.). Bovine factor Xa was supplied by American Diagnostica, Inc. (Greenwich, Conn.). Trypsin, p-nitrophenyl p'-guanidinobenzoate HCl, bovine brain extract, cholesterol, and diacetylphosphate were from Sigma (St. Louis, Mo.). The synthetic substrates, S2444 and S2765 were obtained from diapharma (West Chester, Ohio). Freshly frozen human plasma was purchased from Taipei Blood Center. Mammalian C127 cell- and *E. coli*-derived recombinant TFPIs were prepared as described before (33, 34). Recombinant X-K1 (C-terminal peptide of human factor X fused with the first Kunitz domain of TFPI) (35), and TFPI1-160 were gifts of Dr. George Broze, Jr., (Washington University). Yeast-derived recombinant TAP was a gift from Dr. Dana Abendschein (Washington University).

Cloning of cDNA for Annexin V

ANV cDNA, lacking an initiation Met codon and a stop codon, was generated from human placental mRNA by PCR using ANV reverse primer 1 (5'-ATCAAGCTT ATGCATGTCATCTTCTCCACAGAG-3') (SEQ ID NO: 11) and forward primer 2 (5'-GATCGGAT CCAGTCTG-GTCCTGCTTCACCTT-3') (SEQ ID NO: 12). ATGCAT is the site of restriction enzyme Nsi I used for ligating the 6L15, K$_{APP}$, or KK$_{TFPI22-161}$ gene fragment. ANV cDNA mutation of Cys$^{315}$-to-Ala was created by PCR using oligonucleotide X (5'-CGTGACATGCATGTCATCTTCTCC AGCGAGCA-3') (SEQ ID NO: 13), in which the bolded GC was changed from CA in order to replace the original codon of Cys into Ala. Recombinant ANV was expressed without mutation of Cys$^{315}$. For all other ANV: KPI fusions, ANV cDNA with Cys$^{315}$-to-Ala mutation (SEQ ID NO: 14) was used. The position of Cys/Ala was numbered as 315 in the PCR-amplified ANV cDNA lacking an initiation Met codon.

Construction of 6L15, TAP, and K$_{APP}$ Genes

The synthetic gene encoding 6L 15 was constructed from 3 pairs of overlapping oligonucleotides. The three forward oligomers are:

```
BP-1
(5'-TCCGGACTTCTGCCTGGAACCGCCGTACG    (SEQ ID NO: 15)

ACGGTCCGTGCCGTGCTCTGCACCTGCGTTACT

TC-3');

BP-2
(5'-TACAATGCAAAGGCAGGCCTGTGTCAGAC    (SEQ ID NO: 16)

CTTCTACTACGGCGGTTG CCTGGCTAAGCGT-

3');
and

BP-3
(5'-AACAACTTCGAATCCGCGGAACACTGC      (SEQ ID NO: 17)

ATGCGTACTTGCGGTGGTGCTTA-3').
```

The three reverse oligomers are:

BP-1-3'
(5'-ACGCAGGTGCAGAGCACGGCACGGACCGTC (SEQ ID NO: 18)

GTACGGCGGTTCCAGGCAGAAGTCCGGATGCAT-

3');

BP-2-3'
(5'-AGCCAGGCAACCGCCGTAGTAGAAGGTCTG (SEQ ID NO: 19)

ACACAGGCCTGCC TTTGCATTGTAGAAGTA-

3');;
and

BP-3-3'
(5'-AGCTTAAGCACCACCGCAAGTACGCATGCA (SEQ ID NO: 20)

GTCTTCCGCGGATTCGAAGTTGTTACGCTT-

3');.

The internal oligomers were phosphorylated with $T_4$-polynucleotide kinase. The three complementary oligonucleotide pairs were annealed separately by heating to 95° and slow cooling to room temperature. The annealed oligonucleotide pairs were then ligated with $T_4$-DNA ligase to form 6L15 gene. The NsiI restriction enzyme site ATGCAT was designed in the oligomer sequence of BP-1-3' by changing original codon of $Arg^1$ into His for the ligating to the ANV gene fragment. For expression of 6L15, the original codon of $Arg^1$ was replaced by Ala. The synthetic 6L15 gene consists of the following sequence:

GCT CCG GAC TTC TGC CTG GAA CCG  (SEQ ID NO: 21)

CCG TAC GAC GGT CCG TGC CGT GCT

CTG CAC CTG CGT TAC TTC TAC AAT

GCA AAG GCA GGC CTG TGT CAG ACC

TTC TAC TAC GGC GGT TGC CTG GCT

AAG CGT AAC AAC TTC GAA TCC GCG

GAA GAC TGC ATG CGT ACT TGC GGT

GGT GCT TAA.

The synthetic ala-TAP gene was synthesized from synthetic oligonucleotides according to Neepert et al. (36). The synthetic ala-TAP gene consists of the following sequence:

GCT TAC AAC CGT CTG TGC ATC AAA  (SEQ ID NO: 22)

CCG CGT GAC TGG ATC GAC GAA TGC

GAC TCC AAC GAA GGT GGT GAA CGT

GCT TAC TTC CGT AAC GGT AAA GGT

GGT TGC GAC TCC TTC TGG ATC TGC

CCG GAA GAC CAC ACC GGT GCT GAC

TAC TAC TCC TCC TAC CGT GAC TGC

TTC AAC GCT TGC ATC TAA;

The synthetic $K_{APP}$ gene with flanking sequences was constructed from two pairs of overlapping synthetic oligonucleotides. The two forward oligomers are:

$K_{APP}$-1
(5'-GGCCCTACCCCACAGATACGGAGTTGCCAC (SEQ ID NO: 23)

CACTGAAACTTGAGGTTGTTAGAGAGGTTTGTTC

TGAGCAAGCTGAGACTGGTCCATGTAGAGCTATG

ATTTCTAGATGGTACTTCGACGTT-3');,
and $K_{APP}$-2
(5'-ACTGAGGGTAAGTGTGCTCCATTCTTCTAC (SEQ ID NO: 24)

GGTGGTTGTGGTGGTAACAGAAACAACTTCGACA

CTGAGGAGTACTGTATGGCTGTTTGTGGTTCTGC

TATTTAAATGCATTGATGA-3').

The two reverse oligomers are:

$K_{APP}$-1-3'
(5'-CTCAGTAACGTCGAAGTACCATCTAGAAAT (SEQ ID NO: 25)

CATAGCTCTACATGGACCAGTCTCAGCTTGCTCA

GAACAAACCTCTCTAACAACCTCAAGTTTCAGTG

GTGGCAACTCCGTATCTGTGGGGTAG-3');
and $K_{APP}$-2-3'
(5'-AGCTTCATCAATGCATTTAAATAGCAGAAC (SEQ ID NO: 26)

CACAAACAGCCATACAGTACTCCTCAGTGTCGAA

GTTGTTTCTGTTACCACCACAACCACCGTAGAAG

AATGGAGCACACTTACC-3').

The underlined are complementary sequences coding for the $K_{APP}$ domain. The oligomers were phosphorylated with $T_4$-polynucleotide kinase and annealed by heating to 95° and slow cooling to room temperature. The annealed oligonucleotide pairs were then ligated with $T_4$-DNA ligase. The $K_{APP}$ domain of the synthetic gene consists of the following sequence:

GAG GTT TGT TCT GAG CAA GCT GAG  (SEQ ID NO: 27)

ACT GGT CCA TGT AGA GCT ATG ATT

TCT AGA TGG TAC TTC GAC GTT ACT

GAG GGT AAG TGT GCT CCA TTC TTC

TAC GGT GGT TGT GGT GGT AAC AGA

AAC AAC TTC GAC ACT GAG GAG TAC

TGT ATG GCT GTT TGT GGT TCT GCT

ATT TAA

Construction of E. coli Expression Plasmids

To construct the plasmids for expression of ANV-6L15 and ANV-KK$_{TFPI}$, the following primers were used for PCR amplification and subcloning into pET20b expression vector:

```
ANV-nde     (5'-G GAATTCCATATGGCACAGGTTCTCAGAGG-3')(SEQ ID NO: 28),
ANV-nsi     (5'-CCAATGCATGTCATCTTCTCCAGC-3'))(SEQ ID NO: 29),
6L15-nsi    (5'-CCAATGCATCCGGACTTCTGCCTG-3'))(SEQ ID NO: 30),
KK_TFPI-nsi (5'-CCAATGCATTCATTTTGTGCATTC-3'))(SEQ ID NO: 31),
6L15-sal    (5'-ACGCGTCGACTTA AGCACCACCGCAAG-3')(SEQ ID NO: 32), and
KK_TFPI-sal (5'-ACGCGTCGACTTAGGTTCCATA ATTATCC-3')(SEQ ID NO: 33).
```

The sequence underlined is a Nde I restriction enzyme site and boxed is the cutting site for Sal I. The underlined ATGCAT is Nsi I restriction enzyme site used for gene fusion. The enlarged ATG is the initiation codon of Met and the TTA is a complimentary sequence to the stop codon of TAA. The $KK_{TFP22-161}$ gene fragment was obtained by PCR amplification from a full-length TFPI cDNA clone (34) using primers $KK_{TRPI}$-nsi (SEQ ID 20 NO: 31) and $KK_{TFPI}$-sal (SEQ ID NO: 33). The PCR amplified gene fragment of ANV was digested with NdeI and NsiI restriction enzymes and linked to NsiI and SalI digested 6L15 (or $KK_{TFPI}$) PCR fragment. The fusion gene was ligated into the expression vector of pET20b(+) which was linearized with NdeI and SalI restriction enzymes.

To construct the plasmid for expression of TAP-ANV, the following primers were used for gene fusion and subcloning into pET20b:

```
TAP-nde (5'-GGAATTCCATATGGCTTACAACCGTCTGTG-3')(SEQ ID NO: 34);
TAP-bam (5'-CGGGATCCGATGCAAGCGTTGAAGCAG-3')(SEQ ID NO: 35);
ANV-bam (5'-CGGGATCCGCACAGGTTCTCAGAGGC-3')(SEQ ID NO: 36);
ANV-sal (5'-ACGCGTCGACTTAGTCATCTTCTCCAGCG-3')(SEQ ID NO: 37).
```

The PCR amplified gene fragment of TAP was digested with NdeI and BamHI restriction enzymes and linked to BamHI and SalI digested ANV gene fragment. The fusion gene was inserted into the expression vector of pET20b(+) which was also linearized with NdeI and SalI restriction enzymes.

The desired recombinant plasmids were screened by PCR and DNA sequence determination. The expression plasmids are designated pET20b-AB8, pET20b-AKK11, and pET20b-TAP-A, which expressed intracellularly the recombinant proteins of ANV-6L15 and ANV-$KK_{TFPI}$, and TAP-ANV, respectively, in *E. coli* under the control of T7 promoter.

To express ANV and 6L15 for the purpose of comparison, the PCR-generated gene fragments of ANV and 6L15, respectively, were inserted into the plasmid using the same strategy for *E. coli* expression.

*E. coli* Expression

*E. coli* BL21 (DE3) pLysS [(F⁻ompT $hsdS_B$ ($r_B^-$,$m_B^-$) gal dcm (DE3) pLysS (Cam$^R$)] (Novagene, Madison, Wis.) was used for expression of recombinant proteins. *E. coli* DH5α [(F⁻(Φ80d lacZΔM15) Δ(lacZYA-argF)U169 endA1 recA1 hsdR$^{17}$($r_K^-$-$m_K^+$) deoR thi-1 supE44 gyrA96 relA1 λ⁻)] was used for construction of expression plasmids. The expression plasmid was propagated and isolated from *E. coli* DH5α and was transformed into the frozen competent cells of *E. coli* BL21. A single colony was inoculated into a 25-ml LB broth (containing 100 mg/L ampicillin and 34 mg/L chloroamphenicol), and grown overnight at 37° with vigorous shaking. Ten ml of the overnight culture was inoculated into 1 liter of the same medium in a 2.8 L flask (Nalgene) and maintained at 37° until the $OD_{600}$ of the culture reached 0.5. The culture was induced by adding IPTG (Promega) to a final concentration of 1 mM and continuously shaking at 37° for 4 hours. The *E. coli* cells were harvested by centrifugation at 7000 rpm for 12 min. The cell pellet was frozen at −80° for further use.

Construction of Yeast Expression Plasmid

The *Pichia* expression vector of pPIC9, utilizes the strong and highly inducible $P_{AOX1}$ promoter and α-factor signal peptide for high level expression and secretion of target proteins. The fragment containing the gene of interest was cloned in frame with the secretion signal peptide flanked by Xho I and Not I sites, the sequences from the Xho I site to the initiation codon of the target gene encoding the protease site of KEX2 must be created for occurrence of efficient cleavage of the fusion protein. The primers designed for generating PCR fragment of interest for cloning into vector pPIC9 were ANV-xho (5'- CGC CTCGAGAAAAGA GCA CAG GTT CTC AGA G-3') (SEQ ID NO: 38), $K_{APP}$-not (5'- ATA AGA AT GCGGCCGC TTA AAT AGC AGA ACC AC-3') (SEQ ID NO: 39), ANV-ecov (5'-CGC GATATC ATC TTC TCC AGC GAG-3') (SEQ ID NO: 40), 5'- $K_{APP}$ (5'-GAG GTT TGT TCT GAG CAA GC-3') (SEQ ID NO: 41). The sequences CTCGAG and GCGGC-CGC are Xho I and Not I restriction enzyme sites, respectively, used for editing the gene fragment and ligating into the vector pPIC9. The CTCGAGAAAAGA encoded 4 amino acids, Leu-Glu-Lys-Arg, which is a typical cleavage site for KEX 2 protease, so the following codon in the primer was designed to be the first codon (shown in enlarged text) of the secreted protein of interest. For generating the ANV-$K_{APP}$ fusion gene, we designed primer ANV-ecov which would create EcoRV site (GATATC) located at 3'-end of the ANV gene fragment without changing the last encoded amino acid (Asp). 5'-$K_{APP}$ primer is a forward sequence of $K_{APP}$ gene from the initiation codon of Glu (GAG). The $K_{APP}$ gene fragment amplified by primers 5'-$K_{APP}$ and $K_{APP}$-not was blunt-end ligated to ANV gene amplified by primers ANV-Xho and ANV-ecov and digested by EcoRV to generate the fusion gene of ANV-$K_{APP}$. The fusion gene was digested by Xho I and Not I restriction enzymes and ligated to the pPIC9, which was linearized using the same enzymes. The ligation mixture was transformed into E. coli DH5α and the desired clone was screened by PCR and confirmed by DNA sequence analysis to identify the in frame amino acid sequence along with α-factor signal peptide. The resulting plasmid was pPIC9 ANV-$K_{APP}$.

Pichia Expression

The yeast expression plasmid was propagated and isolated from E. coli DH5α. Integration was targeted by digesting the expression plasmid with Sac I restriction enzyme prior to transformation. The α-factor fused gene cassette including His4 as the selection marker was inserted into the genome of P. pastoris GS115 (his4) at the AOX1 locus via electroporation (37). The recombinant strains were selected by growing from the MD (minimal dextrose medium, 1.34% yeast nitrogen base without amino acid-4×10$^{-5}$% biotin-2% dextrose-1.5% bacto-agar) plate through the His4 compensation.

A single colony of P. pastoris GS115 recombinant strain from the MD plate was inoculated into 2 ml of BMGY medium (buffered glycerol complex medium, 1% yeast extract-2% peptone-100 mM potassium phosphate, pH 6.0-1.34% yeast nitrogen base without amino acid-4×10$^{-5}$% biotin-1% glycerol) in 10 cm long Pyrex tube and grown at 30° with vigorous shaking at 200 rpm overnight until the $OD_{600}$ of the culture reached 2-6. One ml of culture was harvested by centrifugation and resuspended into 3 ml of BMMY medium (buffered methanol complex medium, 1% yeast extract-2% peptone-100 mM potassium phosphate, pH 6.0-1.34% yeast nitrogen base without amino acid-4×10$^{-5}$% biotin-0.5% methanol) in 15 cm long Pyrex tube. The culture was maintained at 30° with vigorous shaking at 200 rpm for 24 hours for expression of the secreted protein. The cells were concentrated by centrifugation at 12,000 rpm for 10 minutes and the supernatant was assayed for inhibitory activity against trypsin. Ten µl of the supernatant was subjected to 12% SDS-PAGE and the expressed ANV-$K_{app}$ was detected by Western blot.

For large-Scale Expression of ANV-$K_{APP}$ in Pichia, a single colony of P. pastoris GS115 recombinant strain from the fresh MD plate was inoculated into 25 ml BMGY medium in a 300-ml flask and was grown at 30° with vigorous shaking at 200 rpm for 2 days. This late log phase culture was used to inoculate 400 ml fresh BMGY medium to a final $OD_{600}$ of 0.1 in 1 L flask. The culture was maintained at 30° until $OD_{600}$ reached 2. The cells were collected by centrifugation at 3000 rpm for 10 minutes in sterilized bottles and resuspended into 1 L of BMMY medium and transferred into 2.8 L flask. The culture was maintained at 30° with shaking to start induction of protein. After 24 hours of induction, the cells were removed by centrifugation and the supernatant was frozen at −80°.

Isolation of Inclusion Bodies from E. coli

Frozen E. coli cell paste was resuspended in cold Milli-Q water at a concentration of 75 mg/ml. The cells were dispersed with a homogenizer for 30 min on ice. The cells were then mechanically lysed by sonication. Lysate was centrifuged at 16,000 g for 20 min. The supernatant was discarded. The inclusion body pellets were collected, resuspended in the same volume of cold Milli-Q water, homogenized, sonicated, and pelleted by centrifugation as above one more time. The inclusion bodies were stored at −80°.

Sulfonation of Inclusion Bodies and Anion Exchange Chromatography

The buffers used for sulfonation, anion exchange chromatography, and protein refolding contained high concentration of urea. Urea solutions were treated with Bio Rad mixed bed resin AG®501-X8 at room temperature for at least 20 min and filtered through 0.2 µm filter before mixing with buffers. One gram of inclusion bodies (wet weight) was dispersed in 40 ml of a solution containing 50 mM Tris/HCl, pH 8.0, and 7.5 M urea by homogenization and vortexing. After the inclusion bodies were largely dissolved, 800 mg of sodium sulfide was added, and the mixture was shaken at room temperature for 30 min. Then, 400 mg of sodium tetracyanate was added and the mixture was shaken at 4° overnight The solution was dialyzed against 400 ml of a solution containing 20 mM Tris/HCl, pH 8, and 4 M urea. The dialyzed solution was centrifuged at 48,000×g for 1 h, filtered through a 0.2 mm filter, and stored at −80°. For anion exchange chromatography, 40 ml of sulfonated and dialyzed sample was loaded onto a HiLoad Q-Sepaharose 16/10 column pre-equilibrated in Q-buffer (20 mM Tris/HCl, pH 8-6 M urea-0.01% Brij 35) containing 0.15 M NaCl at room temperature. The column was washed with 240 ml of equilibration buffer and then eluted with a 396-ml gradient (0.15-0.4 M NaCl) in Q-buffer at a flow rate of 3 ml/min. Nine ml fractions were collected. The peak fractions containing the wanted protein was analyzed by SDS-PAGE, pooled, and used for refolding.

Refold of Disulfide-containing Proteins

A standard refold condition developed for refolding of E. coli-derived TFPI as described previously (34) was used for refolding of Kunitz inhibitors and ANV:KPI fusion proteins. In brief, the sulfonated and anion exchange chromatography pool was diluted to an absorbance of 0.07 at 280 nm with Q-buffer containing 0.3 M NaCl. Solid L-cysteine was added to final concentration of 2 mM. The solution was incubated at room temperature for 24 h, diluted 1:1 with water with addition of 1 mM L-cysteine, and incubated at room temperature for another 24-48 h. For single-domain Kunitz proteins, refold can be carried out at a higher protein concentration (absorbance of 0.15 at 280 nm) with essentially the same results.

Purification of 6L15 and ANV-$KK_{TFPI}$

Refold mixture of 6L15 (18 ml) was acidified to pH 3.0 by titrating with 1 M citric acid, diluted 1:1 with water, and passed thorough a 1×8 cm Q-Sepharose (fast flow) column pre-equilibrated in 20 mM Na-citrate, pH 3.0. The column was then eluted with a gradient from 0.1 to 1 M NaCl in the same buffer. 6L15 was eluted as a symmetrical peak around 0.5 M NaCl.

Refold mixture of ANV-$KK_{TFPI}$ (600 ml) was diluted 1:1 with water and passed through a 1×8 cm Q-Sepliarose (fast flow) pre-equilibrated with 5 mM Tris, pH 8.0-75 mM NaCl. The column was washed with 50 ml of the equilibration buffer. ANV-$KK_{TFPI}$ was then eluted with 5 mM Tris, pH 8.0-0.25 M NaCl.

Purification of TAP-ANV, ANV-6L15, ANV, and ANV-$K_{APP}$.

Refold mixture of TAP-ANV (160 ml) was passed though a 1×8 cm Q-Sepharose (fast flow) column pre-equilibrated in 20 mM Tris, 7.4. The column was washed with 50 ml of the same buffer containing 0.15 M NaCl, and eluted with a gradient from 0.15 M to 0.35 M NaCl in the same buffer.

TAP-ANV was eluted as a single symmetrical peak around 0.33 M NaCl. Refold mixture of ANV-6L15 was loaded on a 1×8 cm Q-Sepharose (fast flow) column pre-equilibrated in 6.7 mM Tris, pH 9.5-2 M urea-0.003% Brij 35-0.1 M NaCl. The column was washed with 40 ml of the same buffer, followed by 30 ml of 20 mM Tris, pH 7.4, then eluted with a 180 ml-gradient from 0.1 M to 1 M NaCl in 20 mM Tris, pH 7.4. ANV-6L15 was eluted at around 0.28 M NaCl. The Q-Sepharose purified TAP-ANV and ANV-6L15 were further purified by adsorption to PS-containing liposomes by modification of the method described by Thiagarajan and Benedict (38). Multilamellar liposomes were prepared according to the method of Kinsky (39). Bovine brain extract (100 mg) containing 50% PS, 150 mg cholesterol, and 10 mg diacetylphosphate were dissolved in chloroform and dried in a stream of nitrogen in a 40-ml glass vial. TBS (10 ml) was added to the vial and agitated vigorously in a vortex mixer for 5 min. The liposome was pelleted by centrifugation at 10,000 g for 10 min. The Q-Sepharose-purified TAP-ANV or ANV-6L15 was added to the liposome and $CaCl_2$ was added to a final concentration of 5 mM. The mixture was incubated at room temperature for 40 min, and then centrifuged at 10,000 g for 10 min. The pellet was washed with TBS-5 mM $CaCl_2$ four times by repeating centrifugation and re-suspension cycle as above. TAP-ANV or ANV-6L15 was eluted from the liposome using a solution containing 10 mM Tris, pH8.0-5 mM EDTA.

Recombinant ANV was directly isolated from *E. coli* lysate by binding to liposomes as described before (38) with some modification. In brief, the *E. coli* pellet was suspended in 50 mM Tris, pH 7.4-10 mM EDTA, and sonicated on ice to obtain lysate. The lysate was stored at −80°. Aliquot of the lysate was thawed, dialyzed against TBS, and clarified by centrifugation at 15,000 g for 30 min. The lysate was incubated with liposome in the presence of 5 mM $CaCl_2$ for 40 min, followed by washing, centrifugation, and EDTA-elution as described above.

Recombinant ANV-$K_{APP}$ was expressed and secrete into the culture medium of *pichia*. The medium was concentrated about 10 fold, exchanged with a buffer containing 10 mM Tris, pH 7.4-0.15 M NaCl, and clarified by centrifugation at 40,000 g for 1 h. The medium concentrate was incubated with liposome in the presence of 5 mM $CaCl_2$, followed by washing, centrifugation, and EDTA-elution as described above. All the proteins eluted from liposomes by EDTA solution were subjected to centrifugation at 20,000 g for 1 h to separate the proteins from majority of the liposomes. To remove residual vesicles, the protein solutions were further filtered through CentriPlus YM-100 (Amicon).

Protein Determination

The concentrations of proteins were determined by absorbance at 280 nm using theoretical extinction coefficients calculated from amino acid sequence data as described by Gill and von Hippel (40). The following molar extinction coefficients were used: ANV (21,050); TAP-ANV (39,550); ANV-6L15 (28,170); ANV-$K_{APP}$ (31,300); ANV-$KK_{TFPI}$ (30,170); TAP (18,500); 6L15 (7,120); C127- and *E. coli*-derived FL-TFPI (20,650); C127 truncated TFPI (19,370); TFPI1-160 (7,840); X-K1 (14,490).

Amidolytic Assays of Trypsini and Factor Xa Inhibitory Activities: Determination of Stoichiometries of Inhibitor-protease Interactions Bovine factor Xa (from American Diagnostica) and porcine trypsin (from Sigma) were titrated with p-nitrophenyl p'-guandininobenzoate according to Smith (41) and Chase and Shaw (42), respectively, to determine the concentrations of active factor Xa and trypsin. Inhibitory activities of TAP, TAP-ANV, and ANV-$KK_{TFPI}$ against factor Xa were assayed by amidolysis of S2765. Ten μl of 50 nM bovine factor Xa in DB-buffer (10 mM Tris, pH7.5-0.15 M NaCl-1 mg/mil BSA-0.002% Tween 20-0.02% $NaN_3$) was mixed with 10 μl inhibitors diluted in the same buffer. After incubation at room temperature for 30 min, 10 μl of the reaction mixture was taken into 96-well plate and mixed with 85 μl of TBS-buffer (50 nM Tris, pH 7.5-0.15 M NaCl-0.02% $NaN_3$) containing 5 mM $CaCl_2$. The absorbance change at 405 nm was recorded on SPECTRAmax® PLUS$^{384}$ (Molecular Devices, Sunnyvale, Calif.) microplate spectrophotometer at room temperature for 60 sec. Stock solution of porcine trypsin was prepared in 50% glycerol-1 mM HCl-20 mM $CaCl_2$ and stored at −20°. Inhibitory activities of 6L15, ANV-6-L15, and ANV-$K_{APP}$ against trypsin were assayed by amidolysis of S2444. A diluted trypsin solution (23 nM) was freshly prepared from the stock in a buffer containing TBS-0.1 mg/ml BSA-20 mM $CaCl_2$. Ten ul of the trypsin solution was mixed with 10 μl of inhibitors diluted in the same buffer in the microplate well. After incubation at room temperature for 10 min, 75 μl of TBS-20 mM $CaCl_2$ and 5 μl of 10 mM S2444 was added to the mixture and the absorbance change at 405 nm was recorded on the microplate spectrophotometer at room temperature for 2 min. In both assays, the fractional activities in the presence of inhibitors were calculated as percentages of that in the absence of inhibitors.

Plasma Clotting Time Assays

Human plasma clotting assays were carried out on an ACL 200 coagulation analyzer (Instrumentation Laboratory, Lexington Mass.). A pooled normal plasma from 4 donors was used. For tissue factor-induced plasma clotting assay, each sample contains 100 μl of pooled plasma mixed with equal volume of an inhibitor dissolved in DB-buffer (10 mM Tris, pH 7.4-0.15 M NaCl-1 mg/ml BSA-0.02% $NaN_3$) at varying concentrations. Inhibitor concentrations were calculated as nanomolar in plasma alone, not final plasma-buffer mixture. Innovin® (recombinant human tissue factor reconstituted with synthetic phospholipids) was diluted 1:100 with PT-buffer (75 mM NaCl-12.5 mM $CaCl_2$-0.5 mg/ml BSA-0.02% NaN3) for the assay. For activated partial thromboplastin time (APTT) assay, each sample contains 180 μl of pooled plasma mixed with 20 μl of an inhibitor dissolved in DB-buffer at varying concentrations. Inhibitor concentrations were calculated as the final concentration in the plasma-buffer mixtures. APTT-SP reagent (Instrumentation Laboratory) was used for the assay without dilution.

Results

Construction and Expression of Recombinant ANV and ANV:KPI Fusions

Plasmid vectors were constructed and used for expression of recombinant ANV and its fusion proteins with various Kunitz-type protease inhibitors possessing specific inhibitory activities against four key coagulation enzymes, factor VIIa, factor IXa, factor Xa, and factor XIa in the clotting cascade. FIG. 2. schematically depicts the molecular structures of these proteins. ANV was expressed as a full-length un-mutated molecule in *E. coli*. For other ANV-KPI fusions, the $Cys^{315}$ of AKV was mutated to Ala to avoid forming disulfide bonds with the cysteines within the Kunitz domains during protein refolding. The fusion protein of TAP-ANV is total of 382 amino acid residues starting with an Ala residue followed by a 60 amino acids of TAP from $Tyr^1$ to $Ile^{60}$, a dipeptide Gly-Ser, and a 319 amino acids of ANV($Cys^{316}$-to-Ala). The fusion protein of ANV-6L15 is total of 378 amino acid residues with a 319 amino acids of ANV ($Cys^{315}$to-Ala) from initial Ala to the final amino acid (Asp) followed by a 60 amino acids of 6L15 from $Met^1$ to $Ala^{60}$. In order to create the NsI restriction enzyme site for gene editing and ligation, the second amino acid of 6L15 in the fusion protein was changed from Ala to His. The fusion protein of ANV-$K_{APP}$ is a polypeptide of 376 amino acids in total length. The N-terminus is the full length ANV($Cys^{315}$-to-Ala) and the C-terminus is a 57 amino acids of $K_{APP}$ polypeptide from $Asp^1$ to $Ile^{57}$. The fusion protein of ANV-$KK_{TFPI}$ is a polypeptide of 459 amino acid residues in length. The N-terminus of this fusion protein is a full length ANV($Cys^{315}$-to-Ala) fused with a 140 amino acid polypeptide starting from Met22 to $Thr^{161}$ of TFPI protein, including Kunitz domains 1 and 2.

Purification of ANV and ANV:KPI Fusion Proteins

Recombinant ANV, TAP-ANV, ANV-6L15, and ANV-$KK_{TFPI}$ were expressed intracellularly in *E. coli*. Essentially all the ANV molecules present in the *E. coli* lysate were capable of binding to PS-containing liposomes in the presence of $Ca^{++}$ when analyzed by SDS-PAGE, suggesting that the expressed protein spontaneously folded itself into active forms. For other *E. coli*-expressed ANV:KPI fusions, majority of the expressed proteins occurred in inclusion bodies and required refolding to obtain active molecules. Using a sulfonation refold process developed previously for TFPI (34), we were able to achieve refolding of ANV:KPI fusion proteins as evidenced from the increase in inhibitory activity against trypsin or factor Xa during refolding. One-step Q-Sepharose chromatography of a refold mixture achieved high degree of purification as a single major band with the expected apparent molecular mass was observed in SDS-PAGE analysis. Further purification was carried out by binding to PS-containing liposomes in the presence of $Ca^{++}$ followed by elution with EDTA. Recombinant ANV-$K_{APP}$ was expressed and secreted into the culture medium of *P. pastoris* in active form. Active ANV-$K_{APP}$ can be purified from concentrated medium by binding to PS-containing liposome in the presence of $Ca^{++}$ and elution with EDTA. SDS-PAGE analysis of the final purified products is shown in FIG. 3. Under non-reducing condition (FIG. 3A), a major band was seen in each preparation. ANV-$KK_{TFPI}$ (lane 2) and ANV (lane 6) both contained traces of dimmers. Under reducing condition (FIG. 3B), the dimers disappeared and the fusion protein bands migrated slightly slower possibly because of disruption of disulfide bonds and unfolding of the Kunitz domains.

Stoichiometries of the Interaction of the Purified Inhibitors with Trypsin or Factor Xa FIG. 4 shows the titrations of trypsin or factor Xa activities by the purified inhibitors. Except ANV-$KK_{TFPI}$, the purified fusion inhibitors (ANV-6L15, TAP-ANV, and ANV-$K_{APP}$) and the Kunitz inhibitors (6L15 and TAP) all inhibits trypsin or factor Xa with apparent stoichiometries of 1:1. These results indicated that all the purified inhibitors containing a single Kunitz domain were substantially pure and fully active. The extent of deviation from 1;1 stoichiometry observed near equimolar concentration of inhibitor and enzyme reflects the variation in affinity of the interactions. The affinities of ANV-6L15, 6L15, and ANV-$K_{APP}$ for trypsin (FIGS. 4A, B, and E) appear stronger and the associations of TAP-ANV and TAP with factor Xa (FIGS. 4C, and D) appear weaker. Evidence of weaker affinities of TAP-ANV and TAP with factor Xa are also inferred from time-dependent slow increases of amidolytic activity upon addition of substrate and buffer in the assay. Titration of Xa with ANV-$KK_{TFPI}$ showed deviation from 1:1 stoichiometry (FIG. 4F). This is possibly due to the weak binding affinity of TFPI-K2 for Xa ($K_i$=90 nM) (43), thus the stoichiometry of interaction cannot be determined under the experimental condition used. Alternatively, the purified ANV-$KK_{TFPI}$ may contain inactive misfolded species.

Prolongation of Tissue Factor-initiated Clotting Time

It is well established that TF is the physiologic trigger of blood coagulation. Therefore, the anticoagulant effects of various inhibitors were examined in TF-initiated plasma coagulation assay. Purified inhibitors were added to pooled human plasma at different concentrations and plasma clotting was initiated by adding a diluted thromboplastin reagent (1:100 dilution of Dade Innovin®). Innovin® is a commercial preparation of recombinant human TF reconstituted with an optimized phospholipid mixtures. The assay reagent contains both TF and anionic phospholipid to allow initiation and propagation of the coagulation cascade, and is a simplified system mimicking plasma clotting in the presence of activated TF-bearing cells/microparticles and platelets. The clotting time of the pooled plasma with added control buffer was 40.7 sec. With increasing concentration of added inhibitors, the clotting time was progressively prolonged. The concentration of inhibitors prolonging the clotting time 1.5 fold (i.e. from 40.7 to 61.1 sec) can be determined from the concentration-clotting time curves. Table 1 shows the concentrations required to prolong clotting time 1.5 fold for various inhibitors and their relative potency ranking. Since TFPI is the most important physiological regulator of the tissue factor pathway of coagulation in blood, and mammalian cell-derived TFPI may resemble most the former, we have chosen recombinant C127 FL-TFPI as a reference standard for comparison. TAP-ANV, presumably targeting the prothrombinase, is 86-fold more potent compare to C127 FL-TFPI. ANV-6L15, designed to inhibit TF/VIIa, is 12 fold more potent than C127 FL-TFPI. ANV-$K_{APP}$ (possibly targeting TF/VIIa, XIa, VIIIa/IXa, and Va/Xa), ANV-$KK_{TFPI}$ (presumably inhibiting TF/VIIa and Va/Xa), and X-$K1_{TFPI}$ hybrid (likely inhibiting TF/VIIa) are 6-7 fold more potent than C127 FL-TFPI. *E. coli*-derived non-glycosylated TFPI and ANV are 2.4 fold more potent than C127 FL-TFPI. TAP has the same potency as C127 FL-TFPI. Kunitz inhibitors alone, as exemplified here by C127 CT-TFPI, TFPI1-160 and 6L15, are 19-, 40- and 86-fold, respectively, less active than C127 FL-TFPI.

Effects of Various Inhibitors on APTT

The anticoagulant effects of various inhibitors were also examined by activated partial thromboplastin time (APTT) assay. APTT measures the intrinsic pathway activity. The effects of various inhibitors in prolonging APTT are shown in FIG. 5. For the purpose of comparison, ANV is chosen as a reference standard. The most potent molecule, TAP-ANV, is about an order of magnitude more potent than ANV. The effect is likely mediated through inhibition of prothrombinase. ANV-$K_{APP}$ (presumably inhibiting XIa, VIIIa/IXa, and Va/Xa), ANV-$KK_{TFPI}$ (presumably inhibiting Va/Xa), and ANV-6L15 (possibly inhibiting kallikrein and XIa) are several-fold more potent than ANV. The Kunitz inhibitors alone (6L15, TAP, and TFPI1-160) are very weak in prolonging APTT. Interestingly, glycosylated mammalian C127 FL-TFPI is about an order of magnitude more potent than non-glycosylated *E. coli*-derived TFPI (FIG. 5), the order of potency being reversed vs. that of tissue factor-induced clotting (Table 1). These results suggest that there are significant differences between mammalian- and *E. coli*-derived TFPIs.

TABLE 1

Effects of various inhibitors on tissue factor-induced clotting time in human plasma.

| Inhibitor | [a][Inhibitor]$_{1.5 \times CT}$, (nM) | [b]Relative potency |
|---|---|---|
| TAP-ANV | 0.80 | 86 |
| ANV-6L15 | 6.0 | 12 |
| ANV-K$_{APP}$ | 9.4 | 7.3 |
| X-K1$_{TFPI}$ | 10 | 6.9 |
| ANV-KK$_{TFPI22-160}$ | 11 | 6.3 |
| *E. coli* ala-TFPI | 19 | 3.6 |
| ANV | 29 | 2.4 |
| TAP | 68 | 1 |
| C127 FL-TFPI[c] | 69 | 1 |
| C127 CT-TFPI[c] | 1300 | 0.053 |
| *E. coli* TFPI1-160 | 2750 | 0.025 |
| 6L15 | 5900 | 0.017 |

[a][Inhibitor]$_{1.5CT}$ is the concentration of inhibitor that prolong the tissue factor-induced clotting time 1.5 fold relative to control (from 40.7 to 61.1 sec) as determined from concentration-dependent clotting time curves for each inhibitor.
[b]Relative potency is calculated from [Inhibitor]$_{1.5CT}$ using mammalian C127 FL-TFPI as reference standard (assigning C127 FL-TFPI as 1).
[c]C127 FL-TFPI refers to full-length molecules; CT-TFPI refers to molecules truncated at the carboxyl terminus as described previously (33).

Although the inventor is not to be bound by theory, it is believed that the foregoing results can be explained and elaborated thereon as follows:

Formation of extrinsic tenase (TF/VIIa), intrinsic tenase (VIIIa/IXa), prothrombinase (Va/Xa) and XIa enzymatic complexes on anionic membrane surfaces are the key processes by which initiation and propagation of the tissue factor pathway of coagulation occur. TFPI is the primary physiological regulator of the initiation of coagulation. TFPI does not directly inhibit TF/VIIa complex per se, but instead, must await generation of factor Xa first before forming an inert quartnary TFPI/Xa/TF/VIIa complex (17). Generation of factor Xa leads to formation of prothrombinase (Va/Xa), and once formed, prothrombinase is protected from inactivation by physiological concentration of TFPI (44,45). During this process, some intrinsic tenase (VIIIa/IXa) is also generated which is not inhibited by TFPI. As a result, TFPI regulates tissue factor pathway in a rather "leaky" manner. In in vitro clotting assay using 1:100 dilution of a commercial thromboplastin reagent, it requires 69 nM of mammalian cell-derived full-length TFPI to prolong clotting time just 1.5 fold (Table 1). In in vivo thrombosis models, efficacies were observed only when high concentrations of TFPI (100-200 nM) are present in circulating blood or topically (18,19,46). These therapeutic doses of TFPI represent about 100-200 fold of that in the normal plasma. The apparent low potency and the large infusion dose required to achieve the desired blood level make TFPI less than ideal for therapeutic applications. Hence, it is highly desirable to have alternative molecules that exert better control of the tissue factor pathway of coagulation. The ANV:KPI fusion proteins created herein are far more potent than TFPI in the inhibition of TF-initiated coagulation and possess other advantages over TFPI as therapeutic anticoagulants.

Coagulation cascade reactions are localized on PS-exposed membrane surfaces that facilitate the assembly of the coagulation complexes and enhance the catalytic efficiency. In the present work, it is hypothesized that enzyme inhibitors that have been conferred the ability to target themselves to the PS-exposed membrane surface would become thrombogenic site-specific and more effective in inhibiting the coagulation complexes. To test this hypothesis, recombinant DNA technology is used to create four fusion proteins that share a common ANV domain linking to different KPI domains (TAP, 6L15, K$_{APP}$, and KK$_{TFPI}$). The ANV moiety has high affinity (K$_d$<0.1 nM) for membranes containing PS (32). The four KPIs chosen for this study have the following inhibition constants (K$_i$) for various coagulation serine proteases: TAP (0.18 nM for Xa) (22); 6L15 (0.2 nM for TF/VIIa, 0.02 nM for plasma kallikrein and 13 nM for XIa) (30,31); K$_{APP}$ (68 nM for TF$_{219}$/VIIa; 13 nM for Xa; 190 nM for IXa; and 0.01 nM for XIa.) (24-27); and K1K2$_{TFPI}$ (90 nM for Xa and 240 nM for TF/VIIa) (43). Based on the specificities of these KPIs, the fusion proteins are presumed to preferentially target various membrane-associated coagulation enzyme complexes as follows: TAP-ANV for Va/Xa; 6L15-ANV for TF/VIIa, kallikrein, and XIa; K$_{APP}$ for XIa, Va/Xa, TF/VIIa, and VIIIa/IXa; and ANV-KK$_{TFPI}$ for Va/Xa and TF/VIIa. In in vitro clotting assays, the KPIs all require fairly high concentrations in plasma to prolong clotting times (30, 47, Table 1 and FIG. 5). All the four ANV:KPI fusion proteins, in contrast, prolong the plasma clotting times at greatly reduced concentrations compared to their component ANV and KPIs (Table 1 and FIG. 5). In both TF-induced plasma clotting and APTT assays, the most potent fusion protein is TAP-ANV. This molecule inhibits prothrombinase since TAP is a highly specific inhibitor of factor Xa. The result is consistent with the finding that factor Xa and prothrombinase generation is the rate-limiting step in the coagulation cascade (3). It is significant to note that 6L15 is a very poor inhibitor of TF-initiated plasma clotting (Table 1) in spite of its high affinity binding with TF/VIIa (K$_i$ 0.2 nM) (30). Thus, high affinity binding of TF/VIIa alone does not correlate with good potency in inhibiting TF-initiated clotting cascade. In contrast, the fusion inhibitor of ANV-6L15 is about three-order of magnitude more potent than 6L15 in inhibiting TF-initiated clotting, indicating that binding to PS greatly facilitates the inhibition of TF/VIIa by 6L15. The four ANV:KPI fusion molecules created herein all show much higher anticoagulant activities than ANV, KPIs, and TFPI as assessed by TF-initiated plasma clotting and APTT assays. Thus, these molecules possess superior anticoagulant potencies to those of the natural anticoagulants.

In vivo animal study has demonstrated that ANV can specifically target and accumulate on platelet-containing thrombi (48). Furthermore, ANV preferentially accumulates at sites of vessel injury and dose-dependently inhibits thrombus formation in arterial and venous thrombosis models (38,49,50). An important attribute of the ANV:KPI fusion proteins described herein is the presence of ANV moiety that confers on them the property of binding specifically to PS with high affinity. Thus, these molecules possess an intrinsic property of targeting themselves to sites of thrombus formation where PS becomes available for assembly of coagulation complexes. Owing to their ability to target thrombogenic sites, it will be feasible to achieve antithrombotic effect without maintaining high levels of these anticoagulants in systemic circulation, thereby minimizing risks of systemic bleeding side effect.

As used herein, the term "pharmaceutically acceptable" refers to a characteristic of carriers, excipients, or other additives commonly used to formulate drug compositions for administration to subjects for the treatment of diseases and conditions.

As used herein the term "subject" refers to both a human or an animal having or suspected of an excess of thrombotic activity.

The terms "effective" and "therapeutically effective" as used herein refer to a characteristic of an amount of a therapeutic compound or composition, wherein when administered to a subject, the amount achieves one or more of the goals of preventing, inhibiting, reducing or eliminating a disease or condition being treated in the subject. With respect to the present application, diseases and conditions amenable to treatment according to the methods and materials provided, include any disease or condition involving an excess of thrombogenesis. Such diseases and conditions include, for example, unstable angina, myocardial infarction, sudden cardiac death, ischemic stroke, ruptured aneurisms, intermittent claudication, critical limb ischemia; deep venous thrombosis, pulmonary embolism, thrombophlebitis, chronic venous insufficiency; surgical thrombosis, prosthetic heart valve, atherosclerosis, restenosis, ischemia reperfusion injury, sepsis, disseminated intravascular coagulation, acute lung injury, malignancy, chronic renal failure, nephrotic syndrome, crescentic glomerulonephritis, diabetes, sickle cell disease, thalassemia, antiphospholipid syndrome, extracorporeal circulation, hemodialysis, peritoneal dialysis, and annexinopathies.

The terms "dosing" and "treatment" as used herein refer to any process, action, application, therapy or the like, wherein a subject, particularly a human being, is rendered medical aid with the object of improving the subject's condition, either directly or indirectly.

The term "therapeutic compound" as used herein refers to a compound useful in the prophylaxis or treatment of a thrombogenesis-related disease or condition.

As demonstrated herein, this series of recombinant proteins can be produced in *E. coli* and yeast. In the *E. coli* system, the proteins can be expressed at very high levels in the inclusion bodies, and active molecules can be obtained by simple refold and purification procedures. In the *Pichia* system, the protein can be secreted into the culture medium in active form and purified by the same simple procedure. From a manufacturing standpoint, ease and low cost of production are of great advantage. However, it is contemplated that other prokaryotic and eukaryotic cell lines can be used as according to well known general molecular biology procedures as described in, for example, in Sambrook, et al., MOLECULAR CLONING—A LABORATORY MANUAL, Second Edition, (Cold Spring Harbor Laboratory, 1989).

Based on the results of the present work, it is believed that other fusion molecules of similar conceptual design can be created. For example: fusion proteins consisting of multiple ANV domains or KPI domains; fusions of ANV with other natural inhibitors of coagulation factors, such as Antistasin, ecotin (51), Acylostoma caninum anticoagulant peptides; fusions of ANV with homologs and variants of KPIs; and fusions of ANV with small-molecule inhibitors of factors VIIa, IXa, Xa, and XIa. In another variation, other PS binding proteins such as other members of annexin family, lacadherin (52), and phospholipid binding moieties of factor V, factor VIII and phospholipase $A_2$ can be used in place of ANV for the creation of fusion molecules. In a further example, disintegrin domains can be linked to ANV or ANV-KPIs to create fusion molecules that inhibit both coagulation reactions and platelet aggregation at sites of thrombogenesis.

All such other examples as will be apparent to the person skilled in the art after reading the present disclosure are intended to be included within the scope of the present invention.

In summary, the newly developed ANV:KPI fusion proteins represent a new class of thrombogenic site-targeted anticoagulants with the following characteristics: (a) They are designed to target TF/VIIa, intrinsic tenase (VIIIa/IXa), prothrombinase (Va/Xa) and XIa associated with PS-exposed thrombogenic membranes; (b) They possess 6-86 fold higher anticoagulant potencies than TFPI, the natural inhibitor of coagulation initiation, in TF-initiated coagulation; (c) Ease and low cost of production, because fully active molecules can be produced by microbial systems and purified by simple $Ca^{++}$-dependent binding to PS-containing liposome followed by elution with a $Ca^{++}$-chelating solution; and (d) Because PS-exposed membranes and associated coagulation complexes are key thrombogenic stimuli at vascular lesions, ANV:KPIs are potentially useful antithrombotic drugs capable of localized passivation of thrombogenic vessel walls and associated thrombi.

REFERENCES

1. Morrissey J H. Tissue factor: An enzyme cofactor and a true receptor. Thromb Haemost 2001; 86: 66-74.
2. Rand M D, Lock J B, van't Veer C, Gaffney D P, Mann K G. Blood clotting in minimally altered whole blood. Blood 1996; 88: 3432-45.
3. Mann K G. Biochemistry and physiology of blood coagulation. Thromb Haemost 1999; 82: 165-74.
4. Hoffman M, Monroe D M, Oliver J A, Roberts H R. Factors IXa and Xa play distinct roles in tissue factor-dependent initiation of coagulation. Blood 1995; 86:1794-801.
5. Monroe D M, Hoffman M, Allen G A, Roberts H R. The factor VII-platelet interplay: effectiveness of recombinant factor VIIa in the treatment of bleeding in severe thrombocytopathia. Sem Thromb Haemost 2000; 26: 373-7.
6. Sims P J, Wiedmer T. Unraveling the mysteries of phospholipid scrambling. Thromb Haemost 2001; 86: 266-75.
7. Zwaal R F A, Comfurius P, Bevers E M. Lipid-protein interactions in blood coagulation. Biochim Biophys Acta 1998; 1376: 433-53.
8. Zwaal R F A, Schroit A J. Pathophysiological implications of membrane phospholipid asymmetry in blood cells. Blood 1997; 89: 1121-32.
9. Dachary-Prigent J, Toti F, Satta N, Pasquet J-M, Uzan A, Freyssinet J-M. Physiopathological significance of catalytic phospholipids in the generation of thrombin. Sem Thromb Hemost 1996; 22: 157-64.
10. Bach R, Rifkin D B. Expression of tissue factor procoagulant activity: Regulation by cytosolic calcium. Proc Natl Acad Sci USA 1990; 87: 6995-9.
11. Le D T, Rapaport S I, Rao L V M. Studies of the mechanism for enhanced cell surface factor VIIa/tissue factor activation of factor X on fibroblast monolayers after their exposure to N-ethylmaleimide. Thromb Haemost 1994; 72: 848-55.
12. Hansen C B, van Deurs B, Petersen L C, Rao L V M. Discordant expression of tissue factor and its activity in polarized epithelial cells. Asymmetry in anionic phospholipid availability as a possible explanation. Blood 1999; 94: 1657-64.

13. Greeno E W, Bach R, Moldow C F. Apoptosis is associated with increased cell surface tissue factor procoagulant activity. Lab Invest 1996; 75: 281-9.

14. Bombeli T, Karsan A, Tait J F, Harlan J M. Apoptotic vascular endothelial cells become procoagulant. Blood 1997; 89: 2429-42.

15. Krishnaswamy S, Field K A, Edgington T S, Morrissey J H, Mann K G. Role of the membrane surface in the activation of human coagulation factor X. J Biol Chem 1992; 267: 26110-20.

16. Bevers E M, Comfurius P, VanRijn J L M L, Hemker H C, Zwaal R F A. Generation of prothrombin-converting activity and the exposure of phosphotidylserine at the outer surface of platelets. Eur J Biochem 1982; 122: 429-36.

17. Broze G J Jr. Tissue factor pathway inhibitor and the current concept of blood coagulation. Blood Coagul Fibrinol 1995; 6: 7-13.

18. Haskel E J, Torr S R, Day K C, Palmier M O, Wun T C, Sobel B E, Abendschein D R. Prevention of arterial reocclusion after thrombolysis with recombinant lipoprotein-associated coagulation inhibitor. Circulation 1991; 84: 821-7.

19. Jang Y, Guzman L A, Linkoff A M, Gottsauner-Wolf M, Forudi F, Hart C E, Courtman D W, Ezban M, Ellis S G, Topol E J. Influence of blockade at specific levels of the coagulation cascade on restenosis in a rabbit atherosclerotic femoral artery injury model. Circulation 1995; 92: 3041-50.

20. Girard T J. Tissue factor pathway inhibitor. In Sasahara A A, Loscalzo J (eds): New Therapeutic Agents in Thrombosis and Thrombolysis. New York, Marcel Dekker, 1997, p 225.

21. Tuszynski G P, Gasic T B, Gasic G J. Isolation and characterization of antistasin. J Biol Chem 1987; 262: 9718-23.

22. Waxman L, Smith D E, Arcuri K E, Vlasuk G P. Tick anticoagulant peptide is a novel inhibitor of blood coagulation factor Xa. Science 1990; 248: 593-6.

23. Stanssen P, Bergum P W, Gansemans Y, Jespers L, Laroche Y, Huang S, Maki S, Messens J, Lauwereys M, Cappello M, Hotez P J, Lasters I, Vlasuk G P. Anticoagulant repertoire of the hook-worm Ancylostoma caninum. Proc Natl Acad Sci USA 1996; 93: 2149-54.

24. Mahdi F, Rehemtulla A, Wan Nostrand W E, Bajaj S P, Schmaier A H. Protease nexin-2/amyloid β-protein precursor regulates factor VIIa and the factor VIIa-tissue factor complex. Thromb Res 2000; 99: 267-76.

25. Schmaier A H, Dahl L D, Hasan A A K, Cines D B, Bauer K A, Van Nostrand W E. Factor IXa inhibition by protease nexin-2/amyloid beta-protein precursor on phospholipid vesicles and cell membranes. Biochemistry 1995; 34: 1171-8.

26. Mahdi F, Van Nostrand W E, Schmaier A H. Protease nexin-2/amyloid beta-protein precursor inhibits factor Xa in the prothrombinase complex. J Biol Chem 1995; 270: 23468-74.

27. Smith R P, Higuchi D A, Broze G J Jr. Platelet coagulation factor XIa inhibitor, a form of Alzheimer amyloid precursor protein. Science 1990; 248: 1126-8.

28. Dennis M S, Lazarus R A. Kunitz domain inhibitors of tissue factor-factor VIIa. I. Potent inhibitors selected from libraries by phage display. J Biol Chem 1994; 269: 22129-36.

29. Dennis M S, Lazarus R A. Kunitz domain inhibitors of tissue factor-factor VIIa. II. Potent and specific inhibitors by competitive phage selection. J Biol Chem 1994; 269: 22137-44

30. Stassen J M, Lambeir A M, Matthyssens G, Ripka W C, Nystrom A, Sixma J J, Vermylen J. Characterization of a novel series of aprotinin-derived anticoagulants. I. In vitro and pharmacological properties. Thromb Haemost 1995; 74: 646-54.

31. Stassen J M, Lambeir A M, Vreys I, Deckmyn H, Matthyssens G, Nystrom A, Vermylen J. Characterization of a novel series of aprotinin-derived anticoagulants. II. Comparative antithrombotic effects on primary thrombus formation in vivo. Thromb Haemost 1995; 74: 655-59.

32. Reutelingsperger C P M, van Heerde W L. Annexin V, the regulator of phosphatidylserine-catalyzed inflammation and coagulation during apoptosis. Cell Mol Life Sci 1997; 53: 527-32.

33. Wun T C, Kretzmer K K, Palmier M O, Day K C, Huang M D, Welsch D J, Lewis C, Wolfe R A, Zobel J F, Lange G W, Frazier R B, Bild G S, Peel M A, Shell R E, Horn N A, Junger K D, Foy B A, Gustufson M E, Leimgruber R M, Novotney W F, Broze G J Jr. Pyla Y E, Hippenmeyer P J, Warren T G. Comparison of recombinant tissue factor pathway inhibitors expressed in human SK hepatoma, mouse C127, baby hamster kidney, and Chinese hamster ovary cells. Thromb Haemost 1992; 68: 54-9.

34. Diaz-Collier J A, Palmier M O, Kretzmer K K, Bishop B F, Combs R G, Obukowicz M G, Frazier R B, Bild G S, Joy W D, Hill S R, Duffin K L, Gustafson M E, Junger K D, Grabner R W, Galluppi G R, Wun T C. Refold and characterization of recombinant tissue factor pathway inhibitor expressed in E. coli. Thromb Haemost 1994; 71: 339-46.

35. Girard T J, MacPhail L A, Likert K M, Novotny W F, Miletich J P, Broze G J Jr. Inhibition of factor VIIa-tissue factor coagulation activity by a hybrid protein. Science 1990; 248: 1421-4.

36. Neeper M P, Waxman L, Smith D E, Schulman C A, Sardana M, Ellis R W, Schaffer L W, Siegl P K S, Vlasuk G P. Characterization of recombinant tick anticoagulant peptide: A highly selective inhibitor of blood coagulation factor Xa. J Biol Chem 1990; 265: 17746-52.

37. Scorer C A, Clare J J, McCombie W R, Romanos M A, and Sreekrishna K. Rapid selection using G418 of high copy number transformants of *Pichia pastoris* for high-level foreign gene expression. Biotechnology 1994; 12: 181-4.

38. Thiagarajan P, Benedict C R. Inhibition of arterial thrombosis by recombinant annexin V in a rabbit carotid artery injury model. Circulation 1997; 96: 233947.

39. Kinsky S C. Preparation of liposomes and a spectrometric assay for release of trapped glucose marker. Methods Enzymol. 1974; 32: 501-514.

40. Gill S C, von Hippel P H. Calculation of protein extinction coefficients from amino acid sequence data. Anal Biochem 1989; 182: 319-26.

41. Smith R L. Titration of activated bovine factor X. J Biol Chem 1973; 248: 2418-23.

42. Chase T Jr, Shaw E. Titration of trypsin, plasmin, and thrombin with p-nitrophenyl p'-guanidinobenzoate HCl. Methods Enzymol 1970; 19: 20-7.

43. Petersen L C, Bjorn S E, Olsen O H, Nordfang O, Norris F, Norris K. Inhibitory properties of separate recombinant Kunitz-type-protease-inhibitor domains from tissue factor pathway inhibitor. Eur J Biochem 1996; 235, 310-6.

44. Mast A, Broze G J Jr. Physiological concentrations of tissue factor pathway inhibitor do not inhibit prothrombinase. Blood 1996; 87: 1845-50.
45. Franssen J, Salemink I, Willems G M, Wun T C, Hemker C, Lindhout T. Prothrombinase is protected from inactivation by tissue factor pathway inhibitor: competition between prothrombin and inhibitor. Biochem J 1997; 323: 33-7.
46. Ozbeck M R, Brown D M, Deune E G, Lantieri L A, Kania N M, Pasia E N, Cooley B C, Wun T-C, Khouri R K. Topical tissue factor pathway inhibitor improves free flap survival in a model simulating free flap errors. J Reconstr Microsurg 1995; 11: 185-188.
47. Schmaier A H, Dahl L D, Rozemuller A J M, Roos R A C, Wagner S L, Chung R, Van Nostrand W E. Protease Nexin-2/Amyloid β protein precursor. A tight-binding inhibitor of coagulation factor IXa. J Clin Invest 1993; 2540-5.
48. Tait J F, Cerqueira M D, Dewhurst T A, Fujikawa K, Ritchie J L, Stratton J R. Evaluation of annexin V as a platelet-directed thrombus targeting agent. Thromb Res 1994; 75: 491-501.
49. Romisch J, Seiffge D, Reiner G, Paques E P, Heimburger N. In vivo antithrombotic potency of placenta protein 4 (annexin V). Thromb Res 1991; 61: 93-104.
50. Van Ryn McKenna J, Merk H, Muller T H, Buchanan M R, Eisert W G. The effect of heparin and annexin V on fibrin accretion after injury in the jugular vein of rabbit. Thromb Haemost 1993; 69: 227-30.
51. McGrath M E, Gillmor S A, Fletterick R J. Ecotin: lessons on survival in a protease-filled world. Protein Sci 1995; 4:141-8.
52. Shi J, Gilbert G E. Lactadherin inhibits enzyme complexes of blood coagulation by competing for phospholipid-binding sites. Blood 2003; 101:2628-36.

---

The invention claimed is:

1. A recombinant anticoagulant protein comprising a protein sequence selected from the group consisting of TAP-ANV (SEQ ID NO:1), ANV-6L15 (SEQ ID NO:2), ANV-K$_{APP}$ (SEQ ID NO:3), and ANV-KK$_{TFP1}$ (SEQ ID NO:4) and conservatively substituted variants thereof exhibiting Kunitz protease inhibitor (KPI) activity.

2. An antithrombotic composition comprising a recombinant anticoagulant protein comprising a protein sequence selected from the group consisting of TAP-ANV (SEQ ID NO:1), ANV-6L15 (SEQ ID NO:2), ANV-K$_{APP}$ (SEQ ID NO:3), and ANV-KK$_{TFP1}$ (SEQ ID NO:4) and conservatively substituted variants thereof exhibiting Kunitz protease inhibitor (KPI) activity.

3. An antithrombotic composition according to claim 2 further comprising a pharmaceutically acceptable excipient.

4. A method of inhibiting blood coagulation in a mammalian subject comprising administering to the subject an effective amount of a recombinant anticoagulant protein comprising a protein sequence selected from the group consisting of TAP-ANV (SEQ ID NO:1), ANV-6L15 (SEQ ID NO:2), ANV-K$_{APP}$ (SEQ ID NO:3), and ANV-KK$_{TFP1}$ (SEQ ID NO:4) and conservatively substituted variants thereof exhibiting Kunitz protease inhibitor (KPI) activity.

* * * * *